United States Patent [19]
Hammerslag

[11] Patent Number: 5,653,730
[45] Date of Patent: Aug. 5, 1997

[54] SURFACE OPENING ADHESIVE SEALER

[75] Inventor: Julius G. Hammerslag, San Juan Capistrano, Calif.

[73] Assignee: Hemodynamics, Inc., San Clemente, Calif.

[21] Appl. No.: 314,049

[22] Filed: Sep. 28, 1994

Related U.S. Application Data

[63] Continuation-in-part of Ser. No. 278,728, Jul. 21, 1994, Pat. No. 5,529,577, which is a continuation of Ser. No. 127,769, Sep. 28, 1993, abandoned.

[51] Int. Cl.$^6$ .................................................. A61B 17/00
[52] U.S. Cl. .......................... 606/214; 606/213; 128/673; 128/748; 128/898
[58] Field of Search .................................... 606/212–214, 606/151, 194, 92–95, 117, 191; 128/673, 672, 748, 898, 899; 604/118, 121, 11–18, 96, 98, 310, 311; 222/510; 401/263

[56] References Cited

U.S. PATENT DOCUMENTS

| | | |
|---|---|---|
| 55,008 | 5/1866 | Gannett. |
| 1,071,063 | 8/1913 | Lee. |
| 1,083,532 | 1/1914 | Grayham. |
| 1,577,465 | 3/1926 | Houge. |
| 2,012,164 | 8/1935 | Gordon. |

(List continued on next page.)

FOREIGN PATENT DOCUMENTS

| | | |
|---|---|---|
| WO/9014810 | 12/1990 | WIPO. |
| WO/9107136 | 5/1991 | WIPO. |
| WO/9221297 | 12/1992 | WIPO. |
| WO/9306878 | 4/1993 | WIPO. |
| WO/9308746 | 5/1993 | WIPO. |

OTHER PUBLICATIONS

*Long Term Pathological Follow–Up of Cerebral Arteriovenous Malformations Treated by Embolization with Bucrylate,* By Harry V. Vinters et al., The New England Journal of Medicine, Feb. 29, 1986 pp. 477–483.

*Primary Examiner*—Jeffrey A. Schmidt
*Attorney, Agent, or Firm*—Knobbe, Martens, Olson & Bear, LLP

[57] ABSTRACT

Disclosed is a device for delivering tissue adhesives and/or sealant patches to a surface which covers or surrounds a lumen, cavity or organ, or potential lumen or cavity, within a human or other animal. Also disclosed is a method of delivering tissue adhesives and/or sealant patches to a surface which covers or surrounds a lumen, cavity or organ, or potential lumen or cavity. The method is particularly suited to sealing perforations in vascular walls, such as after arterial access for Percutaneous Transluminal Coronary Angioplasty (PTCA), Percutaneous Coronary Angiography and Percutaneous Coronary Atherectomy and similar diagnostic and therapeutic procedures.

16 Claims, 11 Drawing Sheets

U.S. PATENT DOCUMENTS

| | | |
|---|---|---|
| 2,388,321 | 11/1945 | Gereke . |
| 2,636,647 | 4/1953 | Covitt et al. . |
| 2,752,920 | 7/1956 | Kurkijian . |
| 3,220,413 | 11/1965 | Sunnen . |
| 3,223,083 | 12/1965 | Cobey . |
| 3,527,841 | 9/1970 | Wicker, Jr. et al. . |
| 3,559,652 | 2/1971 | Banitt et al. . |
| 3,577,516 | 5/1971 | Gould et al. . |
| 3,772,599 | 11/1973 | Robertson et al. . |
| 4,414,976 | 11/1983 | Schwartz et al. . |
| 4,545,374 | 10/1985 | Jacobson . |
| 4,578,055 | 3/1986 | Fischer . |
| 4,606,337 | 8/1986 | Zimmermann et al. . |
| 4,806,614 | 2/1989 | Matsuda et al. . |
| 4,829,099 | 5/1989 | Fuller et al. . |
| 4,909,251 | 3/1990 | Seelich . |
| 4,981,483 | 1/1991 | Akimova et al. . |
| 4,993,948 | 2/1991 | Cameron et al. . |
| 5,011,493 | 4/1991 | Belykh et al. . |
| 5,021,059 | 6/1991 | Kensey et al. ............... 606/213 |
| 5,141,522 | 8/1992 | Landi . |
| 5,156,613 | 10/1992 | Sawyer ............... 606/213 |
| 5,158,542 | 10/1992 | Lazarus . |
| 5,201,712 | 4/1993 | Bryant . |
| 5,201,745 | 4/1993 | Tayot et al. . |
| 5,209,776 | 5/1993 | Bass et al. . |
| 5,219,328 | 6/1993 | Morse et al. . |
| 5,222,939 | 6/1993 | Tiefenbrun ............... 604/59 |
| 5,236,455 | 8/1993 | Wilk et al. . |
| 5,236,563 | 8/1993 | Loh . |
| 5,292,333 | 3/1994 | Johnson ............... 606/213 |
| 5,312,355 | 5/1994 | Lee . |
| 5,324,305 | 6/1994 | Kanner . |
| 5,383,896 | 1/1995 | Gershony et al. . |
| 5,383,897 | 1/1995 | Wholey . |
| 5,391,183 | 2/1995 | Janzen et al. ............... 606/191 |
| 5,395,383 | 3/1995 | Adams et al. ............... 606/151 |
| 5,397,311 | 3/1995 | Walker et al. . |
| 5,431,639 | 7/1995 | Shaw ............... 606/213 |

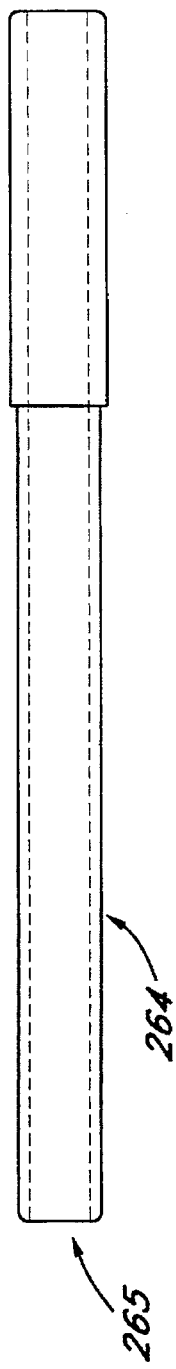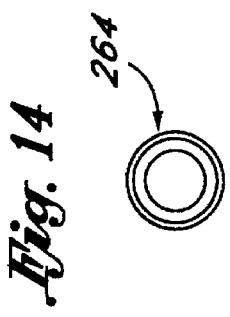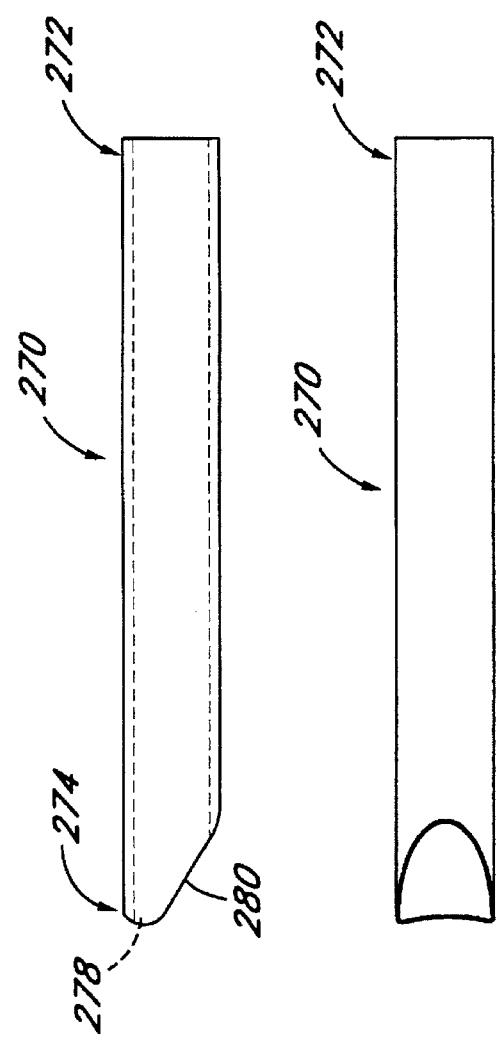
Fig. 13
Fig. 14
Fig. 15
Fig. 16

SURFACE OPENING ADHESIVE SEALER

RELATED CASE

This application is a continuation-in-part of application Ser. No. 08/278,728, filed Jul. 21, 1994, now U.S. Pat. No. 5,529,577 which is a continuation of application Ser. No. 08/127,769, filed Sep. 28, 1993 now abandoned.

BACKGROUND OF THE INVENTION

1. Field of the Invention

This invention relates to a method and an associated device for sealing a puncture in a vessel within mammals. In particular, the invention relates to a method and an associated device for delivering a sealant patch and/or tissue adhesive to seal a puncture in a vessel.

2. Description of Related Art

Percutaneously accessing major vascular structures is a key step in a variety of diagnostic and therapeutic procedures, including Percutaneous Transluminal Coronary Angioplasty (PTCA), Percutaneous Coronary Angiography and Percutaneous Coronary Atherectomy. After the procedure is completed, the instruments used to perform the procedure are withdrawn from the vessel leaving a potential source of bleeding.

The most common method used to prevent post-procedure bleeding at the access site involves the application of direct pressure to the perforation site until normal physiologic pathways have sealed the access site. There are several problems with this method. First, the pressure application technique may fail to prevent hemorrhage. Such a hemorrhage may be life-threatening hemorrhage or lead to a large hematoma. A large hematoma in the groin, for instance, may compromise the major nerve supply to the anterior lower extremity.

Secondly, the pressure application technique extends the length of the in-hospital stay. For example, a PTCA may be completed in 2 to 3 hours, but the patient will typically be hospitalized for several additional hours or overnight, simply to allow the access site to seal physiologically. During this extended hospital stay the patient is required to stay immobile, often with a sand bag taped to his thigh (in the case of femoral artery access).

These complication are exacerbated where PTCA procedures are performed in elderly patients which commonly have arteries with reduced natural elasticity. The access perforation in a relatively inelastic artery does not contract or shrink upon itself to the same extent that would occur with an artery of normal elasticity. The resulting, undeflected perforation in a relatively inelastic artery typically is two to three times larger than an access perforation in a normal artery, further complicating the initiation of hemostasis and the normal physiologic sealing of the access site.

More than 500,000 PTCAs were performed worldwide in 1992 (Cowen Report, March 1993), as well as several times that number of other procedures requiring accessing major vascular structures percutaneously. Thus, the increased length of in-hospital stay necessitated by the pressure application technique considerably increases the expense of procedures requiring such vascular access.

A technique that would allow faster and safer sealing of a vascular access site would save a significant amount of health care resources. There remains a need for such a technique.

SUMMARY OF THE INVENTION

In one aspect, the present invention provides a method of percutaneous transluminal coronary angioplasty and inhibiting arterial bleeding at the arterial perforation site following the procedure which includes the steps of performing the procedure, temporarily inhibiting blood flow through the vessel, exposing the vessel wall surrounding the perforation and applying a tissue adhesive to the vessel wall surrounding the perforation to seal the perforation.

In another aspect, the present invention provides a method of closing a vascular perforation of the type produced during percutaneous transluminal catheterization procedures which includes the steps of exposing the vessel wall surrounding the perforation and applying a tissue adhesive to the surface of the wall surrounding the perforation to seal the perforation.

Further, the invention provides an applicator suitable for percutaneously delivering a tissue adhesive to the surface of a perforated vascular wall and other uses. The applicator includes a tubular housing having a proximal control end of various configurations, a distal delivery end with a delivery surface having a diameter larger than the perforation and a reservoir containing expressible tissue adhesive.

In accordance with another aspect of the present invention, a method of closing a vascular perforation of the type produced during a percutaneous transluminal catheterization procedure is provided. The method involves locating a subcutaneous perforation in a vessel wall and exposing the perforation together with the surface of the wall surrounding the perforation. A sealant patch is applied to the surface of the surrounding wall to seal the perforation. Tissue adhesive preferably bonds the sealant patch to the surface of the vessel wall.

In accordance with a further aspect of the present invention, an applicator which is suitable for percutaneously delivering a sealant patch to the surface of a perforated vascular wall is provided. The applicator includes a housing having a proximal end and a distal delivery end. The housing defines a reservoir for containing a volume of tissue adhesive and a recess for receiving a patch. The applicator also includes a valve which is positioned in the housing between the reservoir and the recess. The valve selectively places the recess in fluid communication with the reservoir. The valve also has an atraumatic delivery surface for applying the sealant patch and tissue adhesive to the surface of the perforated vascular wall. A control, coupled to the valve, controls the expression of adhesive from the reservoir and through the valve to the atraumatic delivery surface of the valve.

BRIEF DESCRIPTION OF THE DRAWINGS

FIG. 2 is a sectional side view of an applicator in accordance with another embodiment of the present invention;

FIG. 2a is a cross-sectional view of the applicator of FIG. 2 taken along lines 2a—2a;

FIG. 6a is a front elevational view of the applicator of FIG. 6 as seen in the direction of line 6a—6a;

FIG. 6b is a cross-sectional view of the applicator of FIG. 6 taken along the line 6b—6b;

FIG. 13 is a side elevational view of an expander cannula.

FIG. 14 is a left end view of the cannula of FIG. 13.

FIG. 15 is a side elevational view of an introducer cannula.

FIG. 16 is a bottom plan view of the introducer cannula of FIG. 15.

DETAILED DESCRIPTION OF THE PREFERRED EMBODIMENTS

As discussed above, there is a need for a technique which will seal a vascular perforation created during a variety of commonly performed diagnostic and therapeutic procedures, including for example, Percutaneous Transluminal Coronary Angioplasty (PTCA), Percutaneous Coronary Angiography and Percutaneous Coronary Atherectomy. In addition, the device and method may have applications in the emergency treatment of trauma, wound closure following surgical procedures and the like. For convenience, the present disclosure will consider primarily the vascular perforation application.

An ideal technique would seal the perforation rapidly, cost effectively and permanently. If used to close a femoral or brachial artery, the technique should result in a seal that can withstand the uppermost potential limits of systolic blood pressure (around 300 mmHg) found in those vessels and the seal should be put in place with an absence of or no more than minimal enlargement of the original percutaneous entrance. One aspect of the present invention addresses the problems inherent in closing a perforation of a vessel, such as, for example, in a femoral or brachial artery following coronary artery or other vessel catheterization by providing a device, and a method that can be used to create a rapid and permanent seal.

Figure 1:
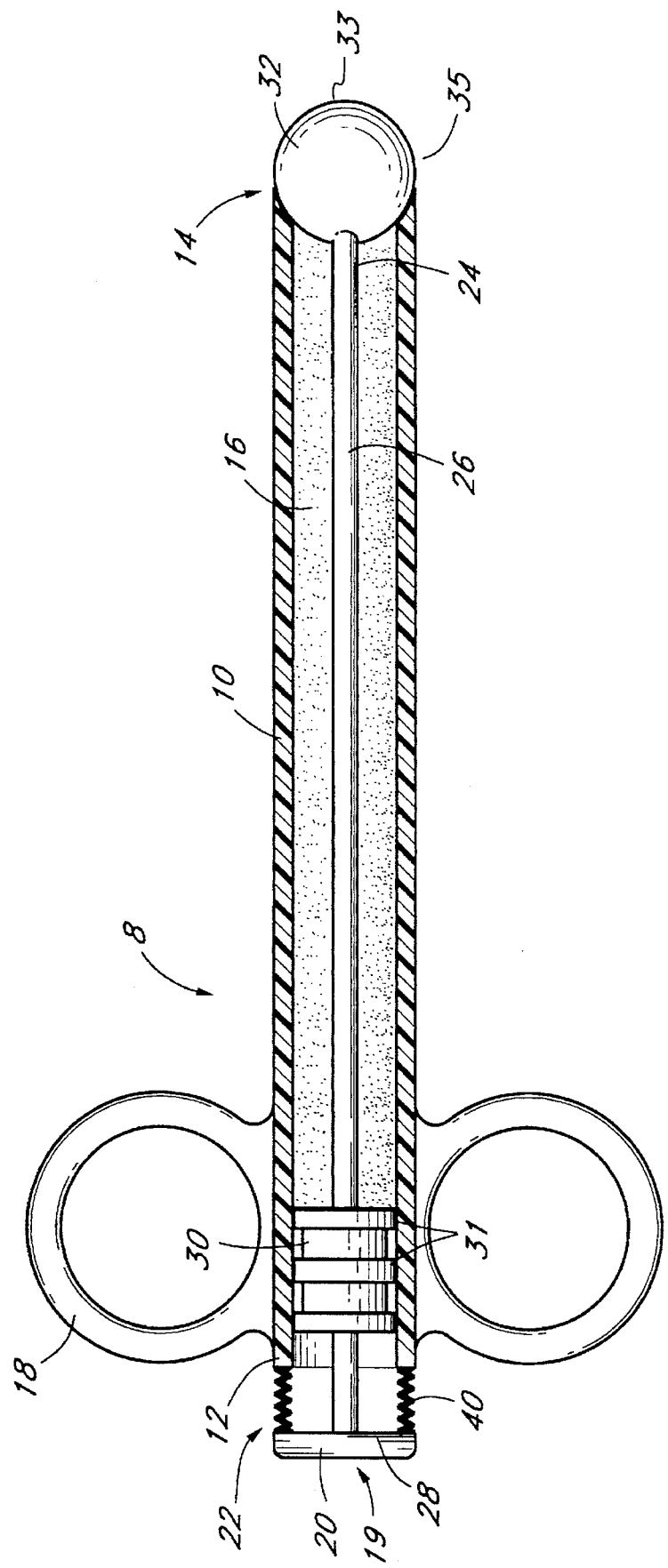
FIG. 1 is a sectional side view of an applicator in accordance with an embodiment of the present invention.

Referring to FIG. 1, there is illustrated one embodiment of the invention for delivering a tissue adhesive to a bodily surface. For convenience, tissue adhesive will be discussed herein, although any of a wide variety of other fluids or fluid-like media can be delivered utilizing the applicator of the present invention. The apparatus of the present invention can also be utilized to deliver materials to any of a wide variety of structures, as will be apparent to one of skill in the art. The present disclosure will discuss embodiments primarily intended for delivery to tissue of the type which covers or surrounds a lumen, cavity or organ, or potential lumen or cavity, within a human or other animal.

The illustrated embodiment comprises an applicator 8 having a generally tubular housing 10 with a proximal control end 12, a distal delivery end 14 and a reservoir 16. Located near the proximal control end 12 are gripping structures, such as a pair of rings 18 to improve the ease of grasping the applicator 8.

A control 19 is provided near proximal end 12 for controllably expressing adhesive from the reservoir 16, as will be discussed. Any of a variety of control structures can be used, such as push buttons, levers, plungers and the like. In addition, a control in the form of a rotating knob may be provided, that functions such that rotation of the knob causes a measured amount of adhesive to be released onto the delivery surface by opening a valve, or consecutively opening and closing a valve, leading from the reservoir. Tactile, auditory or visual feedback or a combination of feedback may be provided as part of the knob control to alert the operator when the measured amount of adhesive has been expressed. Other types of controls will be apparent to one of skill in the art in view of the disclosure herein.

The illustrated control 19 comprises a spring loaded proximal end 22, a distal end 24 and a shaft 26. The proximal end 22 comprises a movable button 20 having a stop 28 of such dimensions or structures that its axial distal travel is limited by the proximal end 12 of the tubular housing 10.

The permissible axial travel of moveable button 20 is determined by the desired volume of adhesive to be expressed upon depression of the button 20. Preferably, the applicator 8 of the present invention is provided in a single unit dose delivery form, so that a single depression of button 20 or a singe activation of another control to its limit causes a single unit volume of adhesive, which has been predetermined at the point of manufacture for an intended application, to be expressed from the distal end 14 of the applicator 8.

For example, in an embodiment of the applicator 8 for use following PTCA arterial perforations, a volume of generally no more than about 1.0 mm$^3$, and preferably no more than about 0.5 mm$^3$ of adhesive will desirably be delivered. Other structures for limiting the delivered volume can be readily incorporated into the applicator 8 by one of skill in the art.

The control 19 is preferably linked to a moveable wall 30 in the reservoir 16. Manipulation of the control 19 advances the moveable wall 30 in a manner that reduces the volume of the reservoir 16, thereby expressing the contents of the reservoir by way of an applicator 32, as discussed below. The moveable wall 30 may comprise a moveable diaphragm, other flexible wall, slidable piston, or other structure for expressing contents from reservoir 16 in response to manipulation of control 19. For instance, as illustrated in FIG. 1, the flexible wall 30 is a slidable piston or plunger with a plurality of annular seals 31 which prevent undesired proximal flow of adhesive from the reservoir 16.

In the illustrated embodiment, adhesive is expressed from the reservoir 16 by way of a valved opening 35 for providing valved fluid communication between the reservoir and the delivery surface 33. Conveniently, the same axial distal motion produced by depression of button 20 both displaces the moveable wall 30 and opens the valve 35 to permit expression of adhesive therethrough.

In this embodiment, the applicator 32 comprises a generally radially symmetrical structure, such as a sphere. The proximal portion of this sphere seats within or against the distal end 14 of tubular body 10, to enclose the reservoir 16 therein. Preferably, a biasing means, such as a spring 40, is provided for biasing the valve 35 in the closed position. Alternative biasing means can also be used, such as polymeric springs and structures which utilize the elastic deformation properties of a plastic material.

Depression of button 20 unseats the applicator 32 from the distal end 14 of housing 10, to provide an annular flow path around applicator 32. Adhesive expressed through valve 35 travels around the applicator 32 to coat a delivery surface 33 generally on the distal portion thereof.

The delivery surface 33 on the applicator 8 can take any of a variety of forms. Optimally, the delivery surface 33 facilitates the application of a substantially uniform coat or layer of adhesive over an area that is larger than the arterial perforation site. In general, forms of delivery surface 33 which reduce the risk of any traumatic injury to the tissue are preferred, such as spherical, or other rounded, blunt tips. A relatively flat distal delivery surface 33 can also be utilized, as will be apparent to one of skill in the art and as discussed below. Alternatively, delivery surface 33 comprises an absorptive blotter material, a permeable membrane or other microporous structure for permitting expression of adhesive directly therethrough.

In general, it is desired that the delivery surface 33 be sufficiently sized relative to the perforation of the vessel wall that the delivery surface 33 will not be penetrable through the perforation unless excessive distal force is applied. In a typical PTCA procedure, the natural elasticity of a major artery wall will normally cause the perforation 60 (FIG. 3) to shrink to about 30% of its original area, upon removal of the procedure instrumentation. This natural shrinkage leaves a vessel wall perforation approximately 1 mm in diameter for relatively elastic, healthy tissue. For the purposes of the present invention, therefore, an applicator 8 having a delivery surface 33 with an effective delivery diameter of at least about 2 mm and preferably a delivery surface of about 3 mm will be utilized.

With this structure, the operator can readily determine through tactile feedback when the delivery surface 33 is securely placed in contact with the vessel wall, yet the risk of perforation through the vessel wall is minimized. This reduces the likelihood that the delivery surface 33 will be introduced into the vessel, which could undesirably introduce adhesive into the bloodstream.

In addition to or as an alternative to reliance upon the size of the delivery surface 33 for limiting distal travel of the applicator 8, other structures, such as distally extending locating pins, radio opaque markers, and the like, can be incorporated into the applicator 8 of the present invention.

Figure 4:
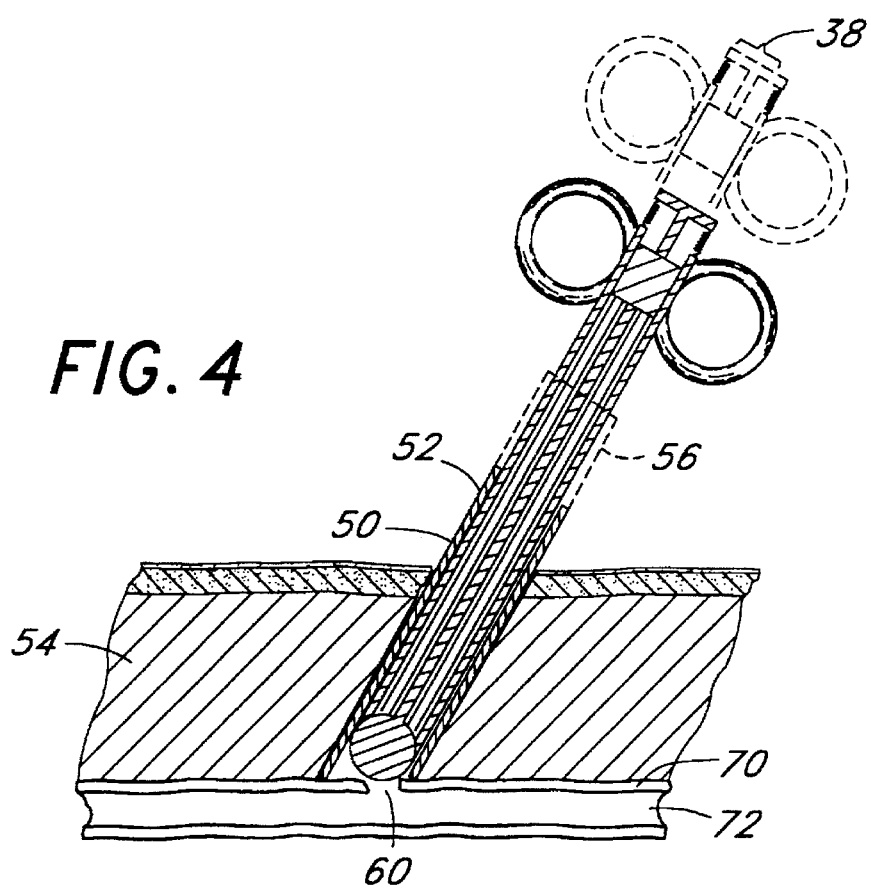

The distal end 14 of the applicator 8 is preferably configured in a manner that minimizes or prevents any contact between the delivery surface 33 and the tissue through which the delivery surface 33 must travel en route to the perforation 60 on the vessel wall. In one embodiment, this is accomplished by introducing the applicator 8 through a tubular introduction cannula 50, as is illustrated in FIG. 4 and will be described infra. In general, the cannula 50 has a sufficient interior diameter to accept the applicator 8, yet a sufficiently small exterior diameter to permit convenient penetration up to the perforated vessel wall.

Preferably, the distal end 54 of the cannula 50 exposes both the perforation 60 and a sufficient area of adjacent vessel wall surrounding the perforation 60 so that a sufficient volume of adhesive can be delivered from delivery surface 33 to the vessel wall. For a typical PTCA arterial perforation 60, having a diameter of about 1 mm, an introduction cannula 50 having an inside diameter of about 3 mm and an outside diameter of about 4 mm at its distal end 54 may conveniently be used.

Figure 3:
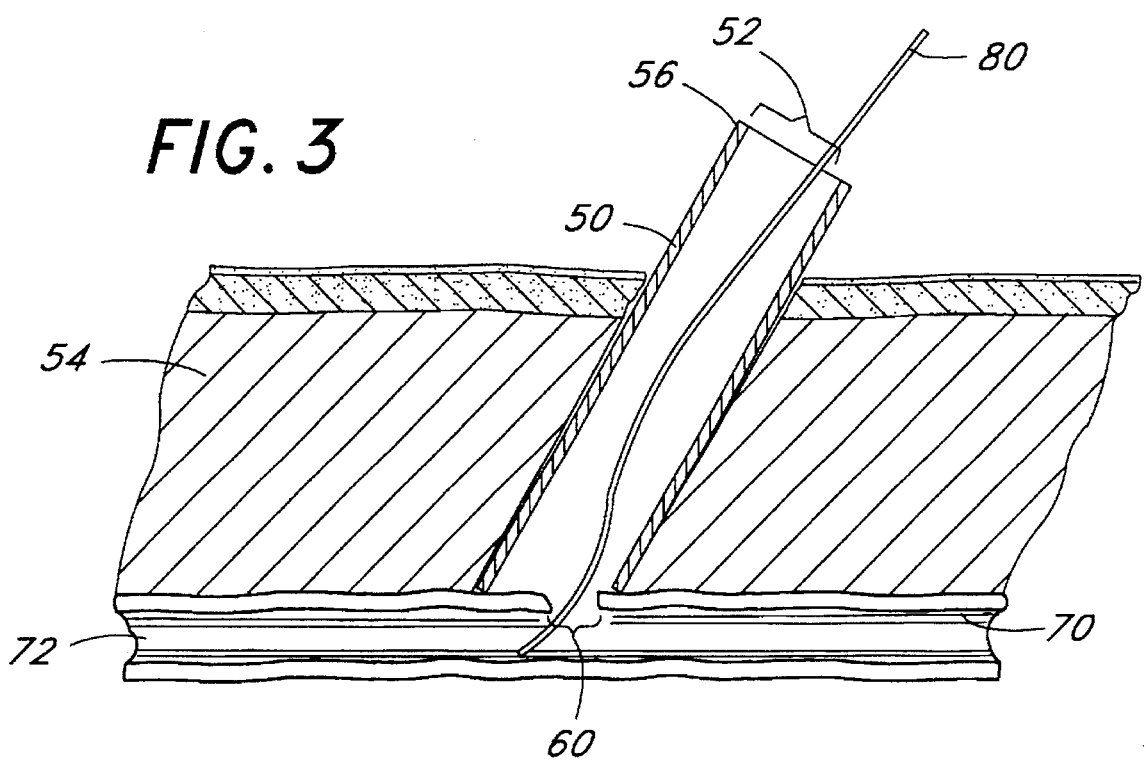
FIGS. 3 and 4 schematically illustrate a series of method steps involved with a preferred treatment method of the present invention.

Alternatively, the function of introduction cannula 50 can be readily accomplished by a structure integrally formed or secured to the applicator 8. For example, the delivery surface 33 can be retractably disposed within an outer tubular housing, as will be readily appreciated by one of skill in the art in view of the disclosure herein. As is illustrated in FIG. 3, the distal end of the cannula 50 or other introduction structure is preferably inclined in a manner that permits uniform contact to the vessel wall while the longitudinal axis of the applicator 8 is inclined at an angle to the vessel wall, which approximates the typical entry angle for the percutaneous perforation.

The reservoir 16 contains any of a variety of tissue adhesives. Suitable adhesives for in vivo use include adhesives within the cyanoacrylate family. In one preferred embodiment, the tissue adhesive comprises one or more of methyl cyanoacrylate, ethyl cyanoacrylate, n-propyl cyanoacrylate, isopropyl cyanoacrylate, n-butyl cyanoacrylate, isobutyl cyanoacrylate, n-amyl cyanoacrylate, isoamyl cyanoacrylate, 3-acetoxypropyl cyanoacrylate, 2-methoxypropyl cyanoacrylate, 3-chloropropyl cyanoacrylate, benzyl cyanoacrylate, phenyl cyanoacrylate, alkenyl cyanoacrylate, butyl-2-cyanoacrylate, alkoxyalkyl 2-cyanoacrylates or fluorinated 2-cyanoacrylates or combinations, thereof. More preferably, the tissue adhesive comprises ethyl cyanoacrylate or butyl-2-cyanoacrylate. These latter two compounds, available from Loctite Corporation (Hartford, Conn.), are normally in a liquid state with water-like viscosity. They harden almost instantaneously upon exposure to atmospheric humidity. Therefore, the reservoir 16 is provided with moisture-tight proximal and distal ends formed by the moveable wall 30 and the proximal end of the applicator 32, to maintain the tissue adhesive in liquid state prior to expression. Preferably, the device is also produced under low humidity conditions and stored in a desiccated package. A removable distal cap (not illustrated) may also be used.

Cyanoacrylate adhesives have been found to harden relatively rapidly when stored below a critical volume of adhesive. Hence, if cyanoacrylate is used, it will be preferable for the reservoir 16 to contain more adhesive than is necessary to seal a typical vascular access site. Preferably, a reservoir volume of at least about 1 to 2 gm is provided to maintain the cyanoacrylate in liquid form in the applicator prior to use. The total volume of adhesive, the desiccation measures and sealing structures on the reservoir 16 can be optimized to produce a desired shelf life by one of skill in the art in view of the disclosure herein.

When used to seal an in vivo tissue surface, cyanoacrylates have several particular advantages. First, they harden almost instantaneously on contact, because of the moisture content of most tissues. For example, they will harden when placed on living vascular walls, and endothelial and mesothelial surfaces. Second, experiments by the inventor indicate that cyanoacrylate sealed vascular punctures can withstand several times the maximum potential systolic pressure, and hence, would not be expected to fail when used to seal a perforation on a vascular wall. Also, cyanoacrylates are naturally thrombogenic. This is an advantage in sealing vascular walls as it promotes the first step in healing the wall. Further, because it seals so rapidly, the risk of embolization or migration can be minimized through the use of the applicators disclosed herein.

Various compounds may be added to the cyanoacrylates to alter the properties of the adhesive. For example, polyacrylic acid having a molecular weight of 200,000 to 600,000 may be cross-linked to the cyanoacrylate to form a suitable biocompatible material. These combination compounds allow the absorbability and resorption rate to be coordinated with the tissue regeneration rate and feature higher elasticity than cyanoacrylates alone. Other additives, such as stabilizers, viscosity modifiers and medications can also be included as desired.

Figures 2, 2A:
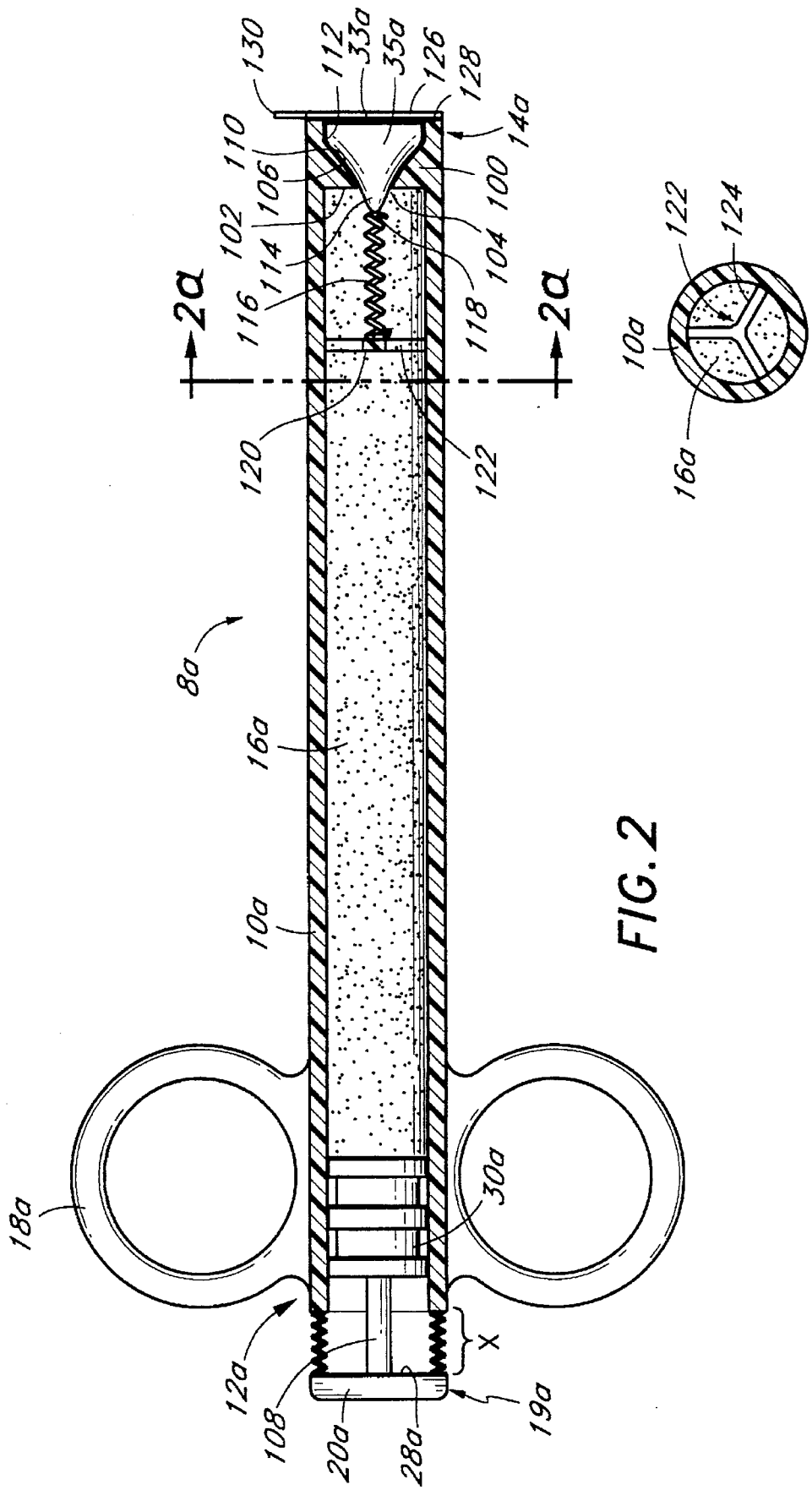

FIG. 2 illustrates another embodiment of the invention for delivering a tissue adhesive to a body surface. For ease of understanding, like reference numerals with an "a" suffix have been used to designate similar elements between the two embodiments.

The applicator 8a has a generally tubular housing 10a with a proximal control end 12a, a distal delivery end 14a and a reservoir 16a. The reservoir 16a desirably contains a tissue adhesive, and preferably contains any of the variety of tissue adhesives described above. As noted above, the reservoir 16a desirably contains more tissue adhesive than is necessary to seal a typical vascular access site in order to maintain the tissue adhesive in a liquid form. It is also contemplated, as noted above, that the reservoir 16a could contain any of a wide variety of other fluids or fluid-like media as well.

The applicator 8a may include grasping structure to ease handling and manipulating the applicator 8a. For this purpose, in the illustrated embodiment, the applicator 8a includes a pair of rings 18a located near the proximal control end 12a of the applicator 8a.

The distal delivery end 14a of the applicator 8a defines an annular valve seat 100 which cooperates with a valve 35a. The valve seat 100 includes a proximal wall 102 which defines an aperture 104 that opens into the reservoir 16a. The aperture 104 has a diameter smaller than that of the reservoir 16a as defined by the tubular housing 10a. The valve seat 100 also includes a sealing surface 106 which preferably tapers, radially outwardly in the distal direction, from the aperture 104 towards the wall of the tubular housing 10a. The surface 106 thus defines generally a frusto-conical shape which mates with a correspondingly shaped surface of the valve 35a, as discussed below. The valve seat 100 also is configured to receive the valve 35a to a sufficient extent that an applicator surface 33a of the valve 35a lies generally flush with or slightly proximally of the distal delivery end 14a of the applicator 8a when the valve 35a is closed (i.e., is seated against the valve seat 100).

As seen in FIG. 2, the applicator 8a also includes a control 19a which controls the expression of adhesive from the reservoir 16a. The control 19a is positioned at the proximal end 12a of the applicator 8a. As with the above-described embodiment, any of a variety of control structures can be used, such as, for example, push buttons, levers, plungers, rotatable knobs, and the like. In the illustrated embodiment, the control 19a includes a plunger 30a disposed within the reservoir 16a. A movable button 20a, attached to the plunger 30a by a stem 108, is provided for actuating movement of the plunger 30a within the reservoir 16a.

A distance X between the proximal end 12a of the tubular housing 10a and a distal surface 28a of the button 20a determines the permissible amount of axial travel of the button 20a and plunger 30a, and hence defines the desired volume of adhesive to be expressed upon depression of the button 20a.

Like the above-described applicator 8 of FIG. 1, the present applicator 8a desirable delivers a single dose of tissue adhesive. The delivered volume of tissue adhesive desirably is predetermined at the point of manufacture for an intended application. It is contemplated that those skilled in the art will really appreciate that any of a variety of volumes of adhesive may be expressed depending upon the particular surgical application.

The valve 35a, disposed at the distal delivery end 14a of the applicator 8a, generally has a conical configuration. The distal end of the valve 35a includes an atraumatic application surface 33a which transitions into a valve surface 110 of the valve 35a by a rounded shoulder region 112. The valve surface 110 of the valve 35a has a generally frusto-conical shape which is sized and configured to mate with the valve seat 100 at the distal end 14a of the tubular housing 10a so as to seal closed the reservoir 16a.

The valve 35a desirably is normally closed. That is, the valve 35a desirably is biased against the valve seat 100. Any of a variety of biasing structures can be used, such as, for example, springs, diaphragms, magnets, and the like. In the illustrated embodiment, a helical spring 116 biases the valve 35a in the proximal direction against the valve seat 100.

In one embodiment, a distal end 118 of the spring 116 passes through a transverse aperture of the valve proximal end 114. The spring 116, however, may be attached to the valve 35a by any of a variety of other means known in the art as well.

The tubular housing 10a includes structure which supports a proximal end 120 of the spring 116. In the illustrated embodiment, the tubular housing 10a includes a spider structure 122 which extends within the tubular housing 10a. As best illustrated in FIG. 2a, the spider structure 122 includes a plurality of legs 124, preferably three legs, which extend from the wall of the housing 10a to the center of the reservoir 16a. The proximal end 120 of the spring 116 is attached to the spider structure 122 in a conventional manner. Alternatively, proximal end 120 of spring 116 is secured directly to the inner surface of the housing 10a.

Activation of the control 19a advances the plunger 30a in the distal direction to compress the adhesive within the reservoir 16a. Once the produced pressure within the reservoir exceeds the biasing force acting on the valve 35a, the valve 35a opens to express adhesive onto the delivery surface 33a.

The delivery surface 33a desirably extends near or beyond the distal delivery end 14a of the housing 10a with the valve 35a opened. In this manner, the delivery surface 33a is positioned to contact the vascular wall surrounding the arterial perforation site. Additionally, the generally blunt configuration of the delivery surface 33a with rounded edges 112 reduces the risk of any traumatic injury to the tissue as well as prevents unintentional penetration or advancement into the vessel, as discussed above.

With reference to FIG. 2, the applicator 8a may also include a release layer 126 which covers the distal delivery end 14a of the tubular housing 10a and the distal delivery surface 33a of the valve 35a. The release layer 126 desirably adheres to the annular distal end surface 128 of the tubular housing 10a and not to the delivery surface 33a. The release layer preferably includes a tab 130 to facilitate removal of the release layer 126 from the applicator 8a. In one embodiment, a small space is provided between the delivery surface 33a and the release layer 126 to permit coating the delivery surface 33a with adhesive prior to removal of the release layer 126. Preferably, the release layer is a transparent polymeric film such as teflon or polyethylene.

In another aspect of the present invention, there is provided a method for delivering a tissue adhesive to a surface which covers or surrounds a lumen, cavity or organ, or potential lumen or cavity, within a human or animal. In one preferred embodiment, the method comprises the steps of providing an applicator having an atraumatic delivery surface, a reservoir and a control for expressing media from the reservoir to the delivery surface.

The delivery surface is placed near or in contact with the tissue surface surrounding an opening therein, and the control is activated to express tissue adhesive from the reservoir to the delivery surface. The delivery surface is thereafter brought into contact or maintained in contact with the vessel wall to deliver a layer of adhesive to the vessel wall. These basic steps are discussed in greater detail below.

This method can be used to close any exposed surface which can be reached by the applicators 8, 8a described above. For example, it has uses in open laparotomy for closing the peritoneal surfaces of the various hollow viscera, diaphragm and omentum. It has potential in sealing the surface of liver and spleen to prevent intraperitoneal hemorrhages. Further, it can be used to seal lung, heart and pleura, as after traumatic, iatrogenic or disease induced perforation.

In another aspect of the present invention, a method is provided for inhibiting arterial bleeding at the arterial access site after Percutaneous Transluminal Coronary Angioplasty (PTCA), Percutaneous Coronary Angiography, Percutaneous Coronary Atherectomy and similar procedures. In this method, access into an artery such as the femoral or brachial is made percutaneously in a manner well known to those with skill in the art. At the conclusion of the procedure, the catheter is withdrawn and pressure applied proximal to the access site to inhibit bleeding. The applicator 8 or 8a, as described above, is advanced through the skin entrance site until the delivery end 14 contacts the vascular perforation 60 and a portion surrounding vascular wall 70. Tissue adhesive is expressed from the delivery end 14 of the applicator 8 and allowed to harden over the perforated tissue, sealing the opening. The applicator 8 is withdrawn and the skin entrance dressed in a usual manner.

Another preferred embodiment of a method for inhibiting arterial bleeding at the arterial access site after catheterization comprises the additional step of positioning the cannula 50 over vascularly indwelling instrumentation, as described below. Before describing this method, a summary of a representative intravascular surgical procedure utilizing a percutaneous opening will be given to further understanding of the invention.

In a representative procedure, an introduction needle is inserted percutaneously into a vascular structure, for example, the femoral artery. A guidewire is passed through the introduction needle to a desired site and the needle is withdrawn leaving the guidewire in position. Next, first and second sheaths, usually an introducer sheath and a dilator sheath, are passed over the guidewire and inserted into the vascular structure. The guidewire and first sheath are removed leaving the second sheath in place. Then the catheter or other instrumentation is inserted through the second sheath and threaded to a desired location, such as an atherosclerotic plaque.

Once the intravascular procedure has been completed, the catheter is removed. The usual method of hemostasis involves also removing the second sheath and applying pressure to the perforation site through the skin until hemostasis has occurred. However, an obturator may be inserted into the second sheath and both obturator and second sheath left in place for a period of time, prior to their removal. This additional step depends on the type of procedure and the patient's state of coagulation among other variables.

Referring now to FIGS. 3 and 4, one application of the present invention is illustrated. A cannula 50, of the present invention, has a proximal end 52, a distal end 54 and a minimum inner dimension 56 greater than the maximum dimension of the perforation 60. Further, the cannula 50 has a minimum inner dimension 56, at the proximal end 54 at least, that is greater than the maximum external dimension 38 of the tubular housing 10. This feature allows the applicator to axially movably fit within the cannula 50.

The cannula 50 may have a smaller inner dimension (not shown) at the distal end 54 than at the proximal end 52 to facilitate placement of the catheter through the skin tract. In this latter embodiment, the inner dimension of the distal end is still large enough to allow the delivery surface 33 of the applicator 8 to contact the portion of the vascular wall 70 surrounding the perforation. The cannula 50 alternatively is provided with a larger internal dimension at its distal end to expose a relatively larger area of vascular surface surrounding the perforation site.

After completing the intravascular surgical procedure, the catheter (not shown) is withdrawn. A guidewire, 80 is placed through the second sheath (not shown) and the second sheath is withdrawn. External pressure is applied proximal (upstream) to the perforation as needed to control bleeding.

The cannula 50 is inserted over the guidewire 80 until the operator obtains tactile feedback that the cannula 50 has contracted the vascular wall 70. FIG. 3 illustrates the placement of the cannula 50 over the guidewire at the point where the cannula contacts the portion of the vascular wall 70 surrounding the perforation.

The guidewire 80 is removed leaving the cannula 50 in position over the perforation 60. Next, the applicator 8 is inserted through the cannula 50 and advanced distally until the delivery surface 33 contacts the vascular wall 70, without penetrating the perforation 60 into the vessel lumen 72. Again the operator will receive tactile feedback indicating that the delivery surface 33 has contacted the vascular wall 70. This step is shown in FIG. 4. Finally, an aliquot of tissue adhesive is expressed from the distal end 33 of the applicator 8, sealing the perforation 60. Both cannula 50 and applicator 8 are withdrawn from the body and a suitable dressing applied. Alternately, the cannula 50 can be withdrawn prior to discharging an aliquot of tissue adhesive.

Cyanoacrylate tissue adhesives will harden virtually on contact, and create a permanent seal. The operator may prefer to express tissue adhesive while the delivery surface 33 is spaced slightly apart from the tissue to be sealed. This permits the adhesive to flow over the delivery surface 33 and produce a relatively uniform coating for application to the target tissue.

Other embodiments will be readily apparent to those with skill in the art. For example, in addition to the above embodiment, the cannula 50 could be introduced over the catheter directly in procedures where the second sheath is withdrawn prior to the catheter. In another embodiment, a guidewire 80 is inserted prior to the withdrawal of the catheter, either through the catheter or between the catheter and the second sheath. The catheter and second sheath would be withdrawn leaving the guidewire and the cannula 50 would be placed as described above. In still another embodiment, the cannula 50 could be introduced over the second sheath rather than through the second sheath.

In yet another embodiment, the guidewire 80 is inserted into the perforation at the conclusion of the procedure. The instrumentation, other than the guidewire 80, is removed. An applicator with a central axially extending guidewire lumen (not illustrated) may then be threaded directly over the guidewire 80 until the distal end of the applicator contacts the portion of the vessel wall surrounding the perforation. The guidewire 80 is then removed and tissue adhesive is controllably expressed to seal the perforation. Finally, the applicator is removed and a suitable dressing applied.

In all cases, bleeding from the perforation site is preferably controlled by applying external pressure proximal (upstream) to the perforation. As described above, the natural elasticity of the vessel wall will normally cause the perforation to shrink, assisting in hemostasis.

Tissue adhesives of the type described above are well suited to seal a typical PTCA arterial perforation, which commonly has a non-dilated diameter of about 1 mm, where the arterial wall is relatively elastic. However, where the arterial wall is relatively inelastic, and the typical PTCA arterial perforation commonly has a non-dilated diameter of about 2–3 mm, it has been found desirable to use a porous patch 150 in combination with the tissue adhesive to further improve the integrity of the seal across the arterial perforation.

Figure 5:
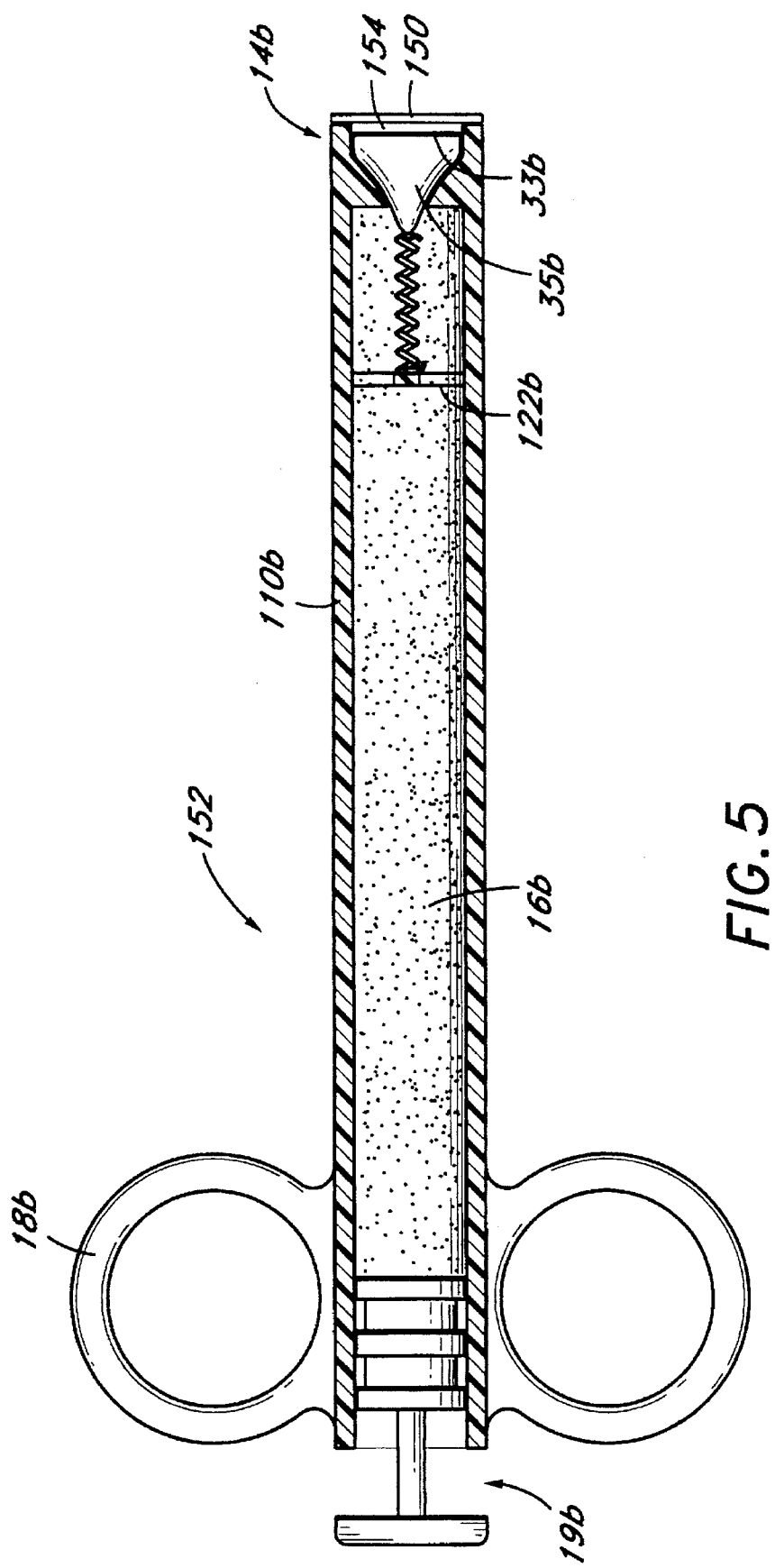
FIG. 5 is a sectional side view of an applicator in accordance with an additional embodiment of the present invention.

Thus, referring to FIG. 5, there has been provided in accordance with another aspect of the present invention an adhesive patch 150 used to seal a perforation in a vessel wall, and, more preferably, to seal a vascular perforation created during any of a variety of commonly performed diagnostic or therapeutic procedures.

The patch 150 desirably has a size larger than the perforation of the vessel (e.g., an artery) and may have any of a variety of shapes depending upon the application of the patch 150. In an illustrated embodiment, the patch 150 generally has a circular shape of a sufficient diameter to completely cover the perforation. It is understood, however, that the size of the patch 150 may only cover a portion of the perforation, yet extend across the perforation so as to attach to the surfaces of the vessel on either side of the perforation. The patch 150 preferably has a diameter of at last about 2 mm and preferably at least about 4 mm for application with a PTCA arterial perforation formed in an inelastic artery.

The patch 150 advantageously is porous so tissue adhesive can flow through the pores of the patch 150 to attach the patch 150 to the ablumenal surface adjacent the perforation and to seal the portion of the patch 150 extending across the perforation. In an exemplary embodiment, the pores have a size of about 300 microns, although it is understood that the pores could have a size ranging between 100µ to 500µ, and more preferably ranging between 200µ to 400µ.

The patch 150 is preferably formed of a mesh, weave or knitted material which is biocompatible, and preferably is biodegradable (i.e., is absorbable within the body). The patch 150 can be formed of any of a wide variety of suitable materials, such as, for example, polytetrafluoroethylene (PTFE), oxidized regenerated cellulose, Gelfilm™ available from the Upjohn Co. and collagen. A suitable material from which to form the patch 150 is a sterile absorbable mesh material (either knitted or woven) available commercially as VICRYL™ from Ethicon (a Johnson and Johnson company) of Somerville, N. J.

The patch 150 may be impregnated, coated, or otherwise pretreated at the point of manufacture with a tissue adhesive, such as, for example, any of the tissue adhesive types described above. In this manner, the adhesive coated surface of the patch 150 will adhere to the surface of the vessel surrounding the perforation upon application of the patch 150. Alternatively, the patch 150 and the tissue adhesive can be provided separately, and the patch 150 is saturated or coated with tissue adhesive at the time of application or just before application, as discussed below.

The patch 150 can be used to seal a puncture site in a viscera or vascular structure by applying the patch 150 and adhesive to the surface of the walls surrounding the perforation to seal the viscera or vascular structure. In order to apply the patch 150 and adhesive over the puncture site, it is desirable to use an applicator which has an atraumatic delivery surface to deliver the adhesive and the patch 150 to the perforation site.

Thus, in accordance with another aspect of the present invention, there is provided an applicator 152 to both deliver adhesive and apply the patch 150 to the perforation site. FIG. 5 illustrates an embodiment of applicator 152 in accordance with a preferred embodiment of the present invention. The applicator depicted by FIG. 5 is substantially identical to that illustrated in FIGS. 2 and 2a and described above. Accordingly, unless indicated otherwise, the above description of the applicator of FIG. 2 will apply equally to FIG. 5, and like reference numerals with a "b" suffix will be used for ease of understanding.

With reference to FIG. 5, the distal delivery end 14b of the tubular housing 10b desirably extends slightly beyond the delivery surface 33b of the valve 35b. The distal delivery end 14b of the tubular housing 10b supports a patch 150. The patch 150 is constructed in accordance with the above description.

The patch 150 also includes on its proximal side around its peripheral edge a light coating of a releasable adhesive, which removably holds the patch 150 on the distal end 14b of the applicator 152 before application. The net release force required to pull the patch 150 from the adhesive should be low enough to permit the patch 150 to adhere to the vascular wall while permitting the applicator 152 to be separated from the patch 150. This can be accomplished in a variety of ways which will be readily apparent to one of skill in the art, including, for example, appropriate adhesive selection, and optimizing the surface area coverage of the adhesive.

The housing 10b defines a space between the patch 150 and the delivery surface 33b of the valve 35b. The space 154 has a sufficient size to allow adhesive expressed through the valve 35b to uniformly coat the patch 150 before application at the perforation site. In an exemplary embodiment, the space 154 has an axial depth ranging between 0.02 and 0.5 mm, and more preferably equal to about 0.1 mm.

A cap (not shown) can cover the distal end of the applicator 152 to protect the patch 150 and to maintain its sterility before application.

Distal movement of the control button 19b causes the valve 35b to open and express adhesive between the distal delivery surface 33b of the valve 35b and the patch 150. Adhesive permeates through the patch 150 to a point of saturation and expresses onto the distal side (i.e., the ablumenal surface) of the patch 150. As discussed more fully below, the patch 150 is thereafter applied over the perforation site. The tissue adhesive will harden virtually on contact to secure the patch 150 over the perforation and to seal the patch 150. The applicator 152 may thereafter be retracted proximally, breaking the connection between the applicator 152 and the patch 150.

Figure 6:
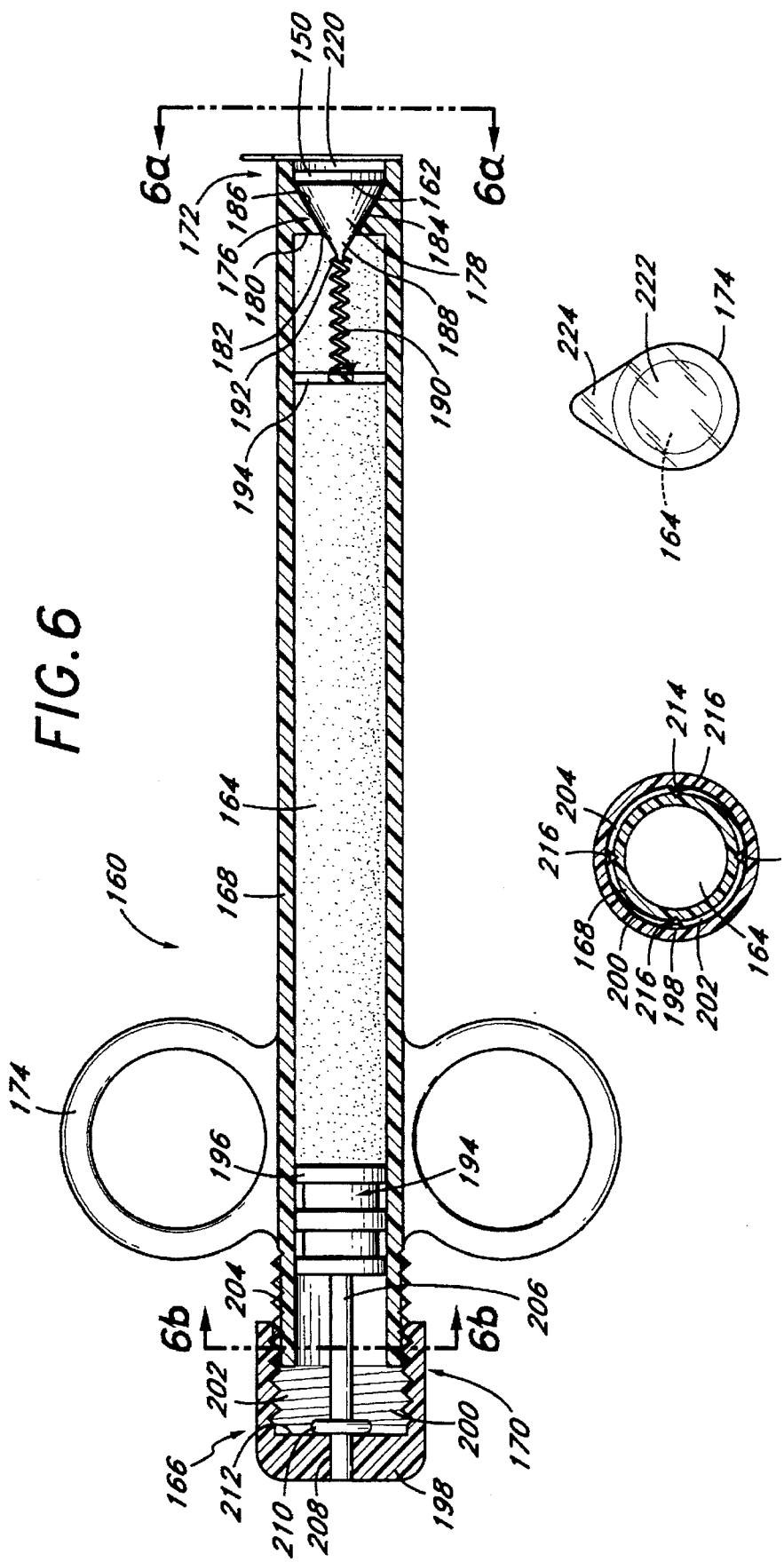
FIG. 6 is a sectional side view of an applicator in accordance with another embodiment of the present invention.

FIG. 6 illustrates another preferred embodiment of an applicator 160 for applying the sealant patch 150, which includes an atraumatic delivery surface 162, a reservoir 164 and a control 166 for expressing media from the reservoir 164 to the delivery surface 162 and the patch 150.

Like the above-described applicators, the present applicator 160 has a generally tubular housing 168 with a proximal end 170 and a distal end 172. The tubular housing 168 defines the reservoir 164. The reservoir 164 desirably contains a tissue adhesive, and preferably contains any of the variety of tissue adhesives described above. It is also contemplated, as noted above, that the reservoir 164 could contain any of a wide variety of other fluids or fluid-like media as well.

Like the above-described applicators, the present applicator 160 desirable delivers a single dose of tissue adhesive. The delivered volume of tissue adhesive desirably is predetermined at the point of manufacture for an intended application. It is contemplated that those skilled in the art will really appreciate that a variety of volumetric sizes of adhesive may be expressed depending upon the particular surgical application. In addition, as noted above, the reservoir 164 desirably contains more tissue adhesive than is necessary to seal a typical vascular access site in order to maintain the tissue adhesive in a liquid form for a suitable product shelf life.

The applicator 160 can also include grasping structures to ease handling and manipulating the applicator 160. For this purpose, in the illustrated embodiment, the applicator 160 includes a pair of rings 174 located near the proximal end 170 of the applicator 160.

The distal end 172 of the applicator 160 defines an annular valve seat 176 which cooperates with a valve 178. As with prior embodiments, the valve seat is conveniently formed by a radially inwardly extending annular ridge. The illustrated valve seat 176 includes a proximal wall 180 which defines an aperture 182 that opens into the reservoir 164. The aperture 182 has a diameter smaller than that of the reservoir 164 as defined by the inner surface of the tubular housing 168.

The valve seat 180 also includes a generally smooth sealing surface 184 which tapers radially outwardly in the distal direction, from the aperture 182 toward the wall of the tubular housing 168. The surface 184 defines generally a frusto-conical shape which mates with a corresponding surface of the valve 178, as discussed below. The valve seat 176 also is configured to receive the valve 178 such that the delivery surface 162 of the valve 178 lies within the tubular housing 168 when the valve 178 is closed (i.e., is seated against the valve seat 176).

The valve 178, disposed at the distal end 172 of the applicator 160, generally has a conical configuration. The distal end of the valve 178 includes the flat or slightly convex delivery surface 162. The valve 178 also includes a generally smooth valve surface 186 which is sized and configured to mate with the corresponding surface of the valve seat 176 so as to seal closed the reservoir. The valve 178 also includes a proximal tip 188 which is provided with a transverse aperture (not shown) for attachment to the spring.

As with the above embodiments, the valve desirably is normally closed, biased against the valve seat 176. Again, any of a variety of biasing structures can be used, such as, for example, springs, diaphragms, magnets and the like. In the illustrated embodiment, a helical tension spring 190 biases the valve 178 in the proximal direction against the valve seat 176.

A distal end 192 of the spring 190 passes through the transverse aperture of the valve proximal end 188 to attach the spring 190 to the valve 178. A spider structure 194, similar to that described above in connection with the embodiment illustrated in FIG. 2, supports a proximal end of the spring within the reservoir 164.

FIG. 6 illustrates an alternate control 166 in the form of a screw knob to control the expression of adhesive from the distal delivery end 172 of the applicator 160. As noted above, however, the control 166 can have a variety of forms, including, but not limited to, a button, plunger, piston, and the like.

In the illustrated embodiment, the control 166 includes a plunger 194 disposed within the reservoir. The plunger 194 includes a plurality of annular seals 196. The diameter of each seal 196 is slightly larger than the inner diameter of the housing 168 such that the seal 196 compresses against the inner wall of the tubular housing 168 when the plunger 194 is inserted into the housing 168. The annular seals 196 are disposed upon the length of the plunger 194 so as to provide a generally labyrinth construction to substantially prevent expression of the adhesive from the reservoir 164 in the proximal direction.

The control 166 also includes a cap 198 which defines a hollow interior cavity 200. The interior cavity 200 carries a series of internal threads 202. The internal threads 202 are sized and configured to engage a series of external threads 204 disposed on the proximal end 170 of the tubular housing 168. The pitch of the threads 202, 204 is chosen to control the volume of adhesive expressed at the distal end 172 of the applicator 160, as discussed below.

A rod 206 connects the screw cap 198 to the plunger 194. In the illustrated embodiment, the rod 206 connects the plunger 194 to the screw cap 198 in a manner which permits the screw cap 198 to rotate with respect to the tubular body 168 without rotating the plunger 194. For this purpose, the screw cap 198 includes a center aperture 208 with a portion of the rod 206 piloted into the aperture 208 to permit rotation of the screw cap 198 about the rod 206. The rod 206 also includes a collar 20 which abuts the proximal surface 212 of the interior cavity 200 to prevent the rod 206 from passing through the aperture 208. It is contemplated, however, that the screw cap 198 and plunger 194 can be directly connected so that the plunger 194 rotates with the screw cap 198.

The distance between the proximal surface 212 of the screw cap interior cavity 200 and the proximal end 170 of the tubular housing 168 limits the amount of adhesive which can be expressed through the valve 178. The screw cap 198 preferably also includes an indexing system, which indicates the extent of travel of the screw cap 178, and thus the volume of adhesive expressed. For instance, the screw cap may be rotated such that at specific intervals of rotation the screw cap snaps or clicks into an index position.

For this purpose, as illustrated in FIG. 6b, the cap 198 may carry one or more tangs 214, which extend radially inward from the threaded inner surface of the interior cavity 200. The tubular body 168 may also include at least one longitudinal groove 216, which releasably receives the tang of the cap 198. In the illustrated embodiment, as the cap 198 is rotated, the tang 214 snaps into the corresponding groove 216 on the tubular housing 168 for each quarter turn of rotation (i.e., 90° rotation) of the screw cap 198.

It is understood that the tubular housing 168 may include more or less longitudinal grooves spaced about the circumference of the housing 168 to indicate specific incremental degrees of rotation. For instance, the housing 168 may include three grooves equally distanced from one another so as to define 120° rotation of the screw cap 198. By selecting an appropriate thread pitch and indexing the degree of rotation, the control 166 can indicate the volume of adhesive expressed at the distal end 172 of the applicator 160.

The volume of adhesive expressed will be equal to the axial displacement of the plunger 194 multiplied by the cross-sectional area of the reservoir 164. The axial displacement of the plunger 194, in turn, is directly proportional to the pitch of the threads multiplied by the number of revolutions of the screw cap 198. Thus, for example, where the thread pitch is 0.5 mm, the number of revolutions of the screw cap 198 is 2, and the cross-sectional area of the reservoir 164 is 28 mm$^2$, the expressed volume of adhesive will be about 28 mm$^3$.

The distal end 172 of the housing 168 defines a cavity 220 in which the patch 150 is received. The patch 150 has a diameter substantially equal to the inside diameter of the cavity 220, and preferably slightly larger than that of the cavity 220 so as to form a slight interference fit with the wall of the cavity 220. The longitudinal length of the cavity 220 is preferably greater than the thickness of the patch 150 such that a small space exists between the patch 150 and the distal end 172 of the tubular housing 168. It is preferred that the patch 150, before application, is positioned within the cavity 220 against the application surface 162 of the valve 178.

At the time of application, the patch 150 desirably is presaturated with tissue adhesive before applying the patch 150 to the perforation site. For this purpose, the cavity 220 has a sufficient size such that a small volume of adhesive can be expressed through the valve 178 and into the distal cavity 220. In an exemplary embodiment, the cavity 220 has a volume of about 1 mm$^3$ with a patch 150 having a thickness of 0.1 mm. The volume of expressed adhesive is sufficient to substantially saturate the sealant patch 150.

A release layer 222 prevents the expressed adhesive from escaping from the distal end 172 of the applicator 168 before application. The release layer 222 desirably adheres to the annular distal end surface of the tubular housing 168 and not to the sealant patch 150. The release layer 222 also includes a tab 224 to facilitate removal of the release layer 222 from the applicator 168. Preferably, the release layer comprises teflon or polyethylene. The release layer 222 is later removed before application of the patch 150 to the puncture site.

To express adhesive into the cavity 220 initially, and onto the applicator surface 186 at the time of application, the controller knob 196 is rotated in a direction which causes the plunger 194 to move distally. Distal movement of the plunger 194 forces the adhesive within the reservoir 164 through the valve seat aperture 182, causing the valve 178 to open. Adhesive expresses through the valve 178 and into the cavity 220. Adhesive fills the cavity 220 and saturates the protective patch 150 contained therein.

As discussed more fully below, the patch 150 is applied over the perforation site. The tissue adhesive will harden virtually on contact to secure the patch 150 over the perforation and to seal the patch.

Figure 7:
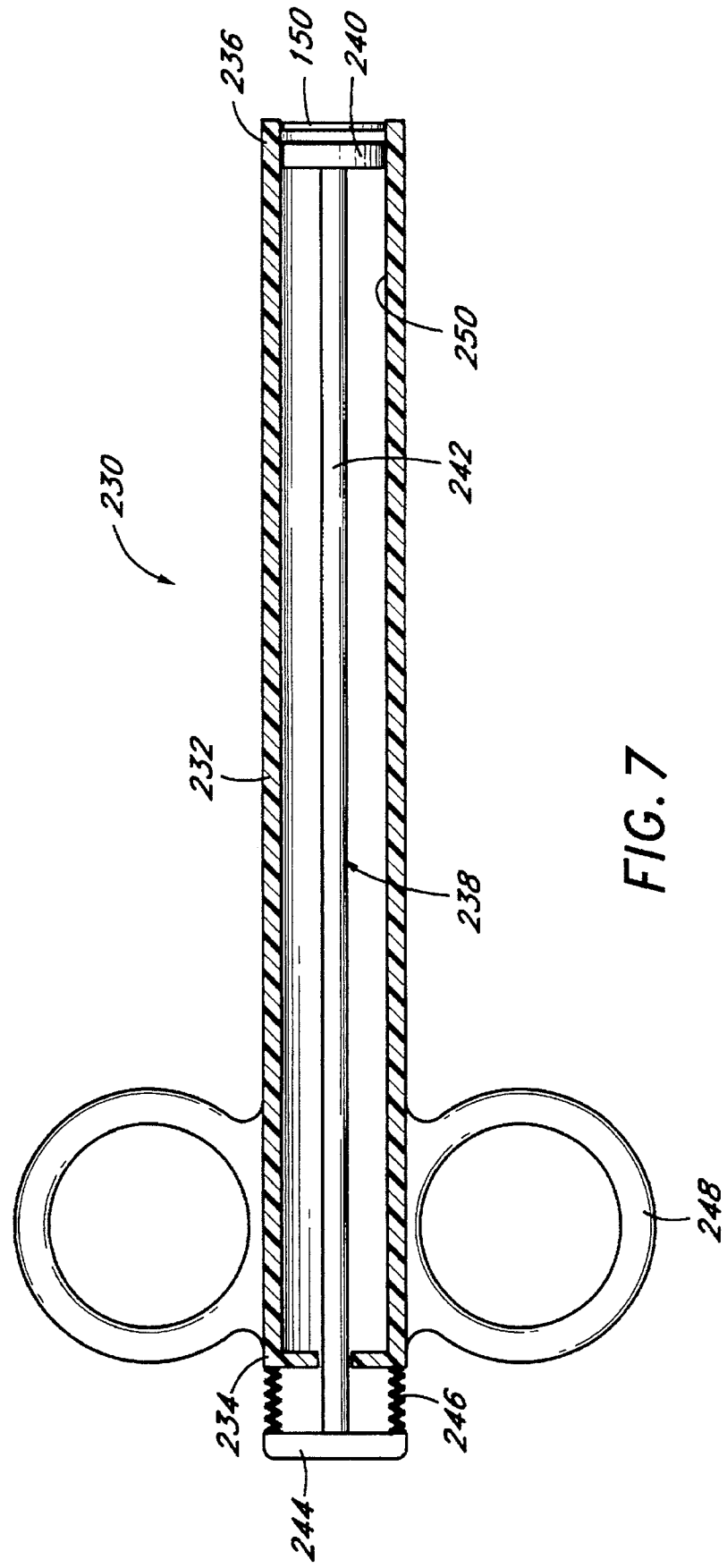
FIG. 7 is a sectional side view of an applicator in accordance with a further embodiment of the present invention.

FIG. 7 illustrates an additional embodiment of an applicator 230 for use with a sealant patch 150 pretreated with a tissue adhesive.

The applicator 230 includes a tubular body 232, having a proximal end 234 and a distal end 236, and an actuator mechanism 238 formed by a distal plunger 240, a linkage rod 242, and a proximal push button 244. Springs or other biasing mechanisms 246 bias the push button 244 to a position spaced from the proximal end 234 of the housing 232.

The applicator 230 also can include gripping structure to ease handling and manipulating the applicator 230. For this purpose, in the illustrated embodiment, the applicator 230 includes a pair of rings 248 located near the proximal end 234 of the applicator 230. It is understood that other types of conventional gripping structures could be used as well.

A sealant patch 150, of the type described above, is disposed at the distal end 236 of the applicator 230. The sealant patch 150 has a diameter substantially equal to the diameter of the tubular housing 232, and more preferably slightly larger so as to form a slight interference fit within the interior wall 250 of the applicator housing 232. Alternatively, radially inwardly directed ridges or other surface structures can removably retain the patch 150 as will be appreciated by one of skill in the art.

The sealant patch 150, as noted above, may be precoated with an adhesive which hardens virtually on contact with tissue to permanently bind the sealant patch 150 to the tissue over the puncture site. Any of the variety of tissue adhesive discussed above can be used. It also is contemplated that an adhesive coating may be applied to the ablumenal side of the patch 150 just before application. Preferably, with most cyanoacrylate adhesives, adhesive will be applied to the patch just prior to the implantation of the patch.

The application of the adhesive coating can occur by direct application of the adhesive to the patch 150, by dipping the distal end of the applicator 230 into a reservoir of adhesive, or by contacting the patch 150 with fluid permeable membrane or absorptive blotter material saturated with adhesive.

In operation, the delivery end 236 of the applicator 230 is placed near or in contact with the tissue surface surrounding an opening therein, and the control 244 is activated to dislodge the adhesive patch 150 from the distal end 236 of the applicator 230. The patch 150 is placed in contact with the tissue surface over the perforation site.

As noted above, this method can be used to close any exposed surface which can be reached by any of the above-described applicators. For instance, the above-described applicators may be used in open laparotomy for closing the peritoneal surfaces of various hollow viscera, diaphragm and omentum. The sealant patch 150 applied by the applicator also has the potential of sealing the surface of the liver or spleen, or used to seal perforated lungs, hearts, or pleura. It may also be used to seal a perforation of a vascular lumen, such as an artery or vessel.

In this latter application, the present invention also includes a preferred method for inhibiting arterial bleeding at the arterial access site after percutaneous transluminal procedures, such as, for example, angioplasty, angiography, coronary angiography, atherectomy, or similar procedures.

FIGS. 8 through 12 schematically illustrate a series of method steps involved with a preferred method of inhibiting arterial bleeding at the arterial access site. For illustrative purposes, this method will be described as involving the use of an applicator comprising an elongate body with an angled patch surface on its distal end to conform to the surface of the artery. However, it is understood that other types of applicators, including the other embodiments described above, for delivering adhesive alone or a patch, can be used as well.

In a representative PTCA procedure, the position and axial orientation of a vascular structure, for example, the femoral artery, is determined tactily using three adjacent finger tips. An introduction needle is inserted at about 30° into the artery using finger pressure against the artery upstream of the puncture to stop blood flow.

A short introduction guidewire is passed through the introduction needle and into the artery and the needle is withdrawn leaving the guidewire in position. Next, first and second sheaths, usually an introducer sheath and a dilator sheath, are passed over the guidewire and inserted into the vascular structure as is well known. The dilator sheath is removed leaving the introducer sheath in place to provide arterial access. A guidewire is threaded through the sheath and transluminally to the desired treatment location. Then the balloon catheter or other instrumentation is inserted through the introducer sheath and threaded over the guidewire to a desired location, such as an atherosclerotic plaque.

Once the intravascular procedure has been completed, the catheter is removed. The usual method of hemostasis involves also removing the introducer sheath and guidewire, and applying pressure to the perforation site through the skin until hemostasis has occurred. Alternatively, an obturator may be inserted into the introducer sheath and both obturator and introducer sheath left in place for a period of time, prior to their removal. This additional step depends on the type of procedure and the patient's state of coagulation among other variables.

Referring to FIGS. 8 through 12, arterial catheterization commonly involves perforating a wall 260 of the vessel 262 such as, for example, the femoral artery, by introducing a needle percutaneously into the vascular structure. Various sheaths, catheters or other instrumentation are introduced through that puncture, as desired, to accomplish the medical procedure. Following the procedure, the guidewire and/or a tubular introduction sheath can be left in the artery to permit the puncture closure method of the present invention.

Figure 8:
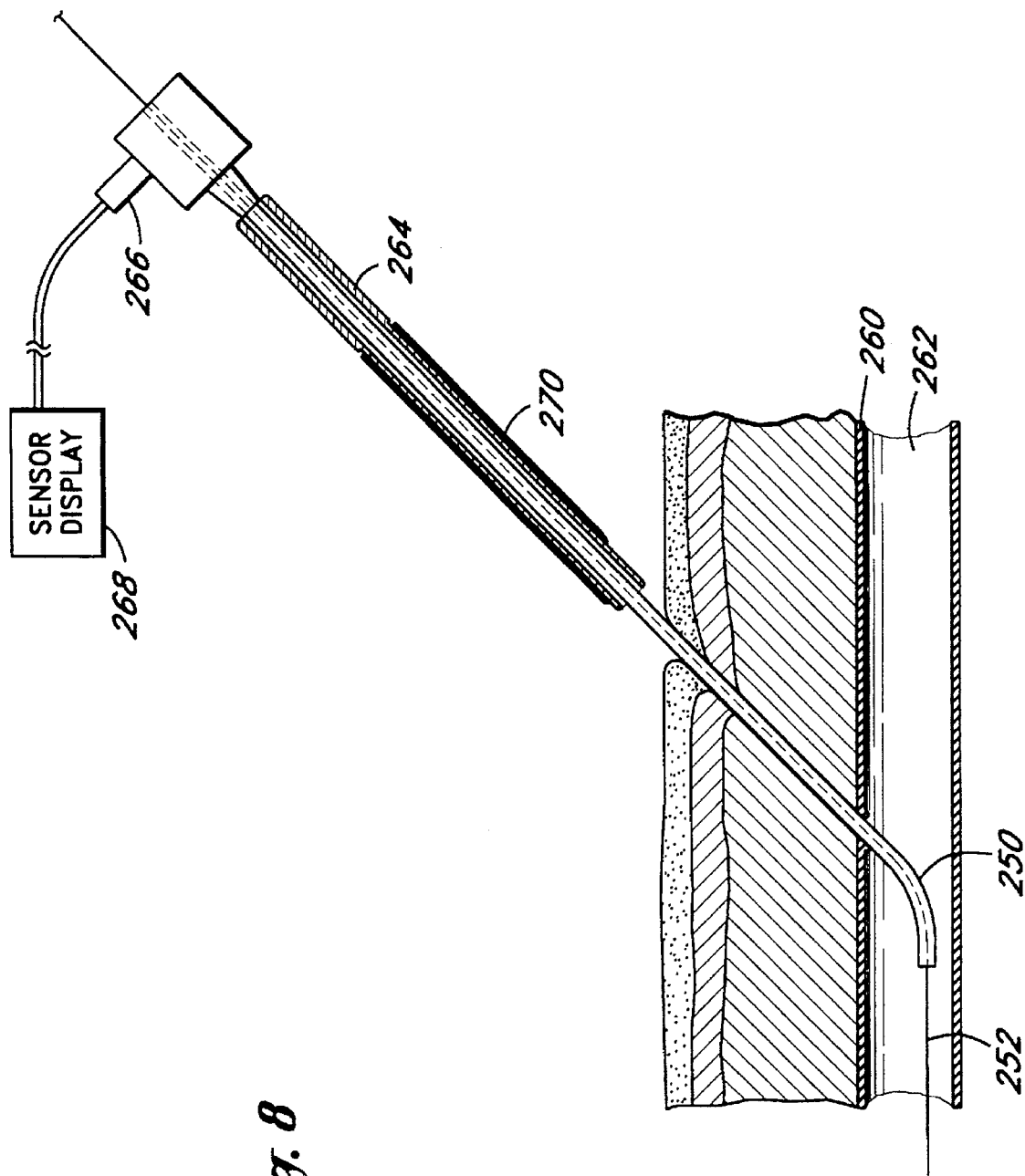
FIG. 8 is a schematic representation of a catheter introduction sheath having a tissue expander cannula and introducer cannula thereon, in position within an artery.

With reference to FIG. 8, an introducer sheath 250 having a guidewire 252 extending there through is in position within the vascular structure 262. The introducer 250 may have been left in place following the vascular catheterization procedure, or may have been introduced subsequently for the purpose of the present vascular patching procedure.

During catheterization procedures, blood pressure is commonly measured at the arterial access site. As seen in FIG. 8, a pressure sensor display 268 is connected to a side port 266 on the introducer 250.

As illustrated in FIG. 8, the tubular sheath 250 is in one embodiment of the present invention modified by carrying an expander cannula 264 having a introducer cannula 270 slidably mounted thereon. The expander cannula 264 and introducer cannula 270 in this embodiment are mounted on the sheath 250 prior to commencement of the catherization procedure. In this embodiment, the catherization (e.g. balloon dilatation, drug delivery etc.) is conducted through the sheath 250 having the expander cannula 264 and introducer cannula 270 thereon throughout.

In an alternate embodiment of the invention, the expander cannula 264 is provided in two halves, and adapted to be mounted upon the sheath 250 at the clinical site. If the physician prefers the maneuverability of the sheath 250 without the expander cannula 264 and introducer cannula 270 thereon, he can use a standard cannula 250 for the catherization procedure. At the completion of that procedure, a two or more part expander cannula 264 is reassembled around the introducer sheath 250, and advanced distally along the sheath 250 in accordance with the procedure discussed below. Once the expander cannula 264 is in position against the outer wall of the artery as discussed below, the sheath 250 may be removed, and the distal end of the introducer cannula 270 is advanced over the proximal end of the expander cannula 264 and distally until it is appropriately positioned against the wall of the artery. At that time, the expander cannula 264 can be removed proximally leaving the introducer cannula 270 in place, and ready for the adhesive or adhesive patch application as discussed below.

The split expander cannula of the present invention can be manufactured in a variety of ways, as will be apparent to one of skill in the art. For example, the expander cannula described above and illustrated in FIGS. 15 and 16 can be cut in two halves along an axially extending plane. Preferably, releasable interlocking structure are provided for retaining the two halves in an assembled configuration. For example, pins can be provided on one half of the expander cannula for engaging corresponding recesses on the other half of the cannula. Any of a variety of "snap fit" interlocking structures can be utilized, to accomplish the advantages of the present invention.

Preferably, unlike the embodiment illustrated in FIGS. 15 and 16, the split expander cannula is provided with a substantially uniform outside diameter throughout its entire length. This facilitates mounting the distal end of the introducer cannula over the proximal end of the expander cannula, so that the introducer cannula can be advanced distally along the expander cannula into the appropriate position such as that illustrated in FIG. 10.

Although the split expander cannula described above is described in terms of two opposing halves, the expander may be constructed from any of a variety of pieces which are reassembleable over the sheath into a generally tubular structure. Thus, three or more axially extending segments can be provided for reassembly into a unitary tubular structure. In the preferred embodiment, two halves are provided, which may be snapped fit together at both contact points. Alternatively, the two halves may be joined by an axially extending hinge such as a section of flexible material, so that the hinged expander halves can be positioned around the sheath 250 and then closed thereon to form a tubular expander.

With reference to the embodiment illustrated in FIG. 8, the introducer 250 is withdrawn from the vascular structure 262 to a location where its distal end is adjacent to the ablumenal surface of the vessel wall 260. See FIG. 9. The blood pressure display 268 aids in the proper positioning of the introducer 250 at this location. A surgeon, or like operator, slowly withdraws the introducer 250 from the vessel while monitoring the blood pressure displayed by the blood pressure display 268. The blood pressure significantly drops once the distal end of the introducer 250 is completely withdrawn from the vessel and the perforation shrinks to its nondilated size. In this manner, the operator knows when he or she has withdrawn the distal end of the introducer 250 to a position adjacent to the ablumenal surface of the vessel 262 as illustrated in FIG. 9.

Figure 9:
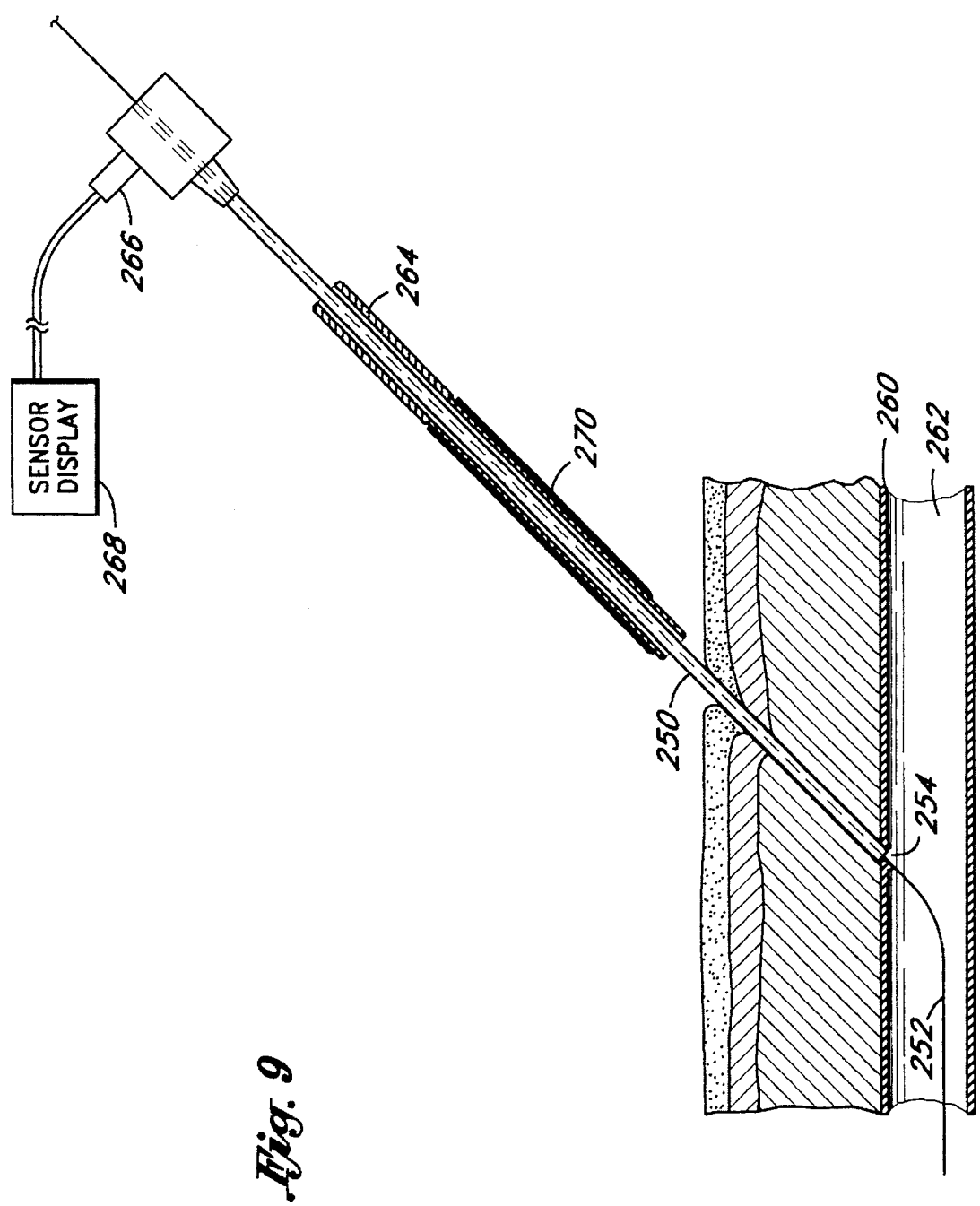
FIG. 9 is a schematic illustration as in FIG. 8, with the catheter introduction sheath withdrawn from the artery.
Figure 10:
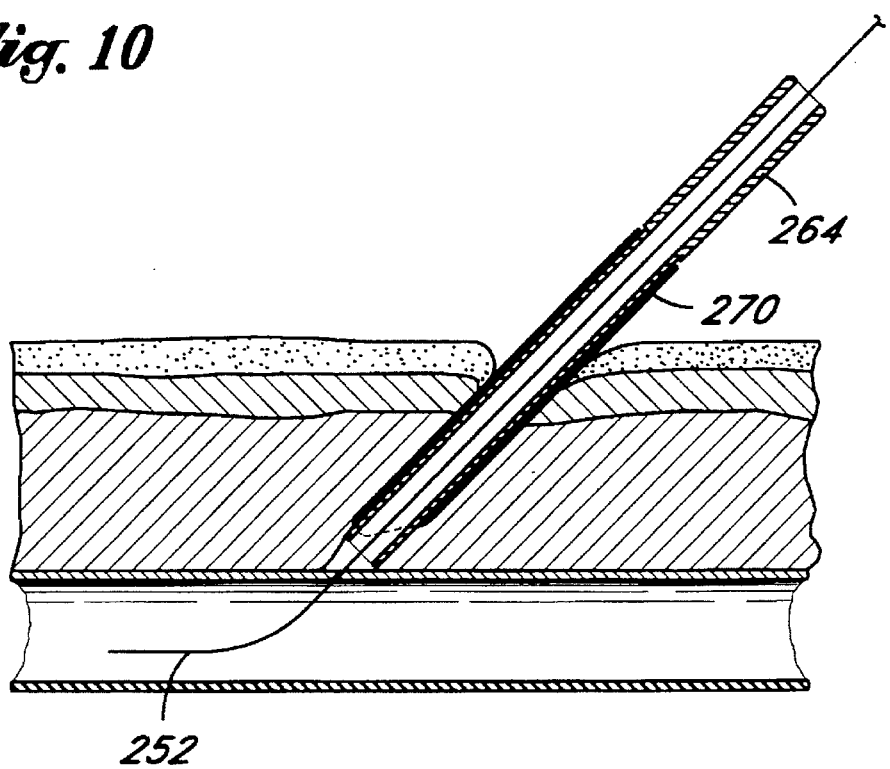
FIG. 10 is a schematic representation as in FIG. 9, with the introducer cannula and expander cannula in position against the artery wall.
Figure 11:
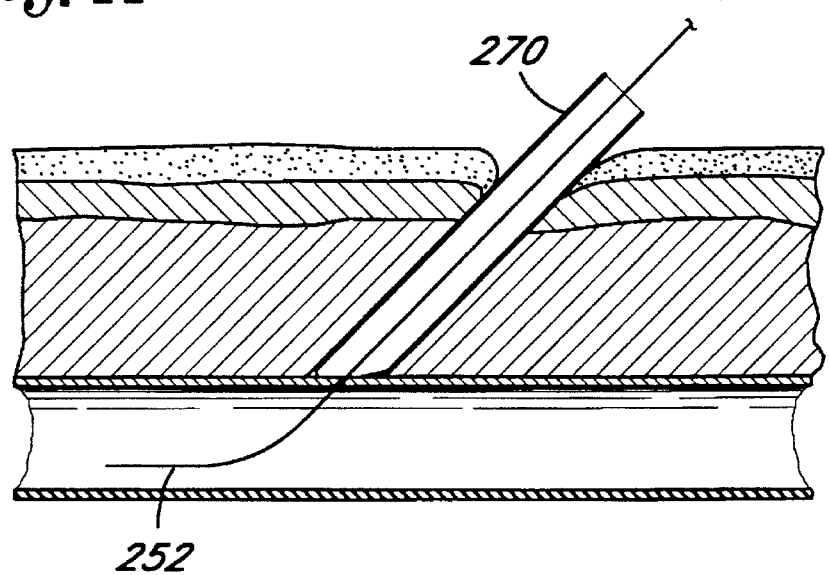
FIG. 11 is a schematic representation as in FIG. 10, with the expander cannula removed.

With reference to FIGS. 9–11, the assembly of the expander cannula 264 and introducer cannula 270 is advanced distally along the catherization sheath 250, until the distal end 265 of the expander cannula 264 contacts the vessel wall. Contact with the vessel wall can be determine by tactile feedback to the operator. Alternatively, indium such as a line or other marking drawn around the outer circumference of the sheath 250 can be positioned such that it becomes visible to the operator when the expander cannula 264 has been advanced sufficiently distally that the distal end 265 of expander cannula 264 is at the surface of the vessel.

Once the distal end 265 of expander cannula 264 is in position against the exterior wall of the vessel 262, the sheath 264 can be removed to produce the assembly schematically illustrated in FIG. 10. Preferably, the guidewire 265 remains in place.

In the illustrated embodiment, once the introducer cannula 270 is seated against the vessel wall, the expander cannula 264 may be proximally withdrawn, to produce the assembly illustrated schematically in FIG. 11. In an alternate embodiment, the function of the expander cannula 264 and introducer cannula 270 can be combined into a single device. A variety of specific structural modifications can be made, in view of the disclosure herein, by one of ordinary skill in the art in view of the objective to properly positioning the introducer cannula 270 against the vessel wall.

One embodiment of an introducer cannula 270 and dilator cannula 264 is shown in FIGS. 13–16. The cannula 270 has a proximal end 272, a distal end 274, and a minimum inner diameter, which is greater than the maximum diameter of the perforation 276 in the vessel wall 260. The cannula 270 also desirably has a minimum inner diameter, which is greater than the maximum external diameter of the patch applicator 80 or adhesive applicator. This feature allows the patch and/or adhesive applicator to axially, movably fit within the cannula 270.

Preferably, the distal end 274 of cannula 270 is provided with an atraumatic tip 278 to minimize damage to the vessel or surrounding tissue. Distal end 274 is preferably also provided with an angled cut 280 which facilitates placement against the vessel wall at an introduction angle of about 30°.

Preferably, the distal end 274 of the cannula 270 has a sufficient diameter to expose both the perforation 254 and a sufficient area of adjacent vessel wall surrounding the perforation 254 so that a sufficient overlap by the patch can be achieved. For a typical PTCA arterial perforation 254, having a diameter of about 1 mm, an introduction cannula 270 having an inside diameter of about 3 mm and an outside diameter of about 4 mm at its distal end 265 may conveniently be used.

Alternatively, the function of introducer cannula 270 can be readily accomplished by a structure integrally formed or secured to the applicator 80. For example, the delivery surface 86 can be retractably disposed within an outer tubular housing, as will be readily appreciated by one of skill in the art in view of the disclosure herein.

Figure 12:
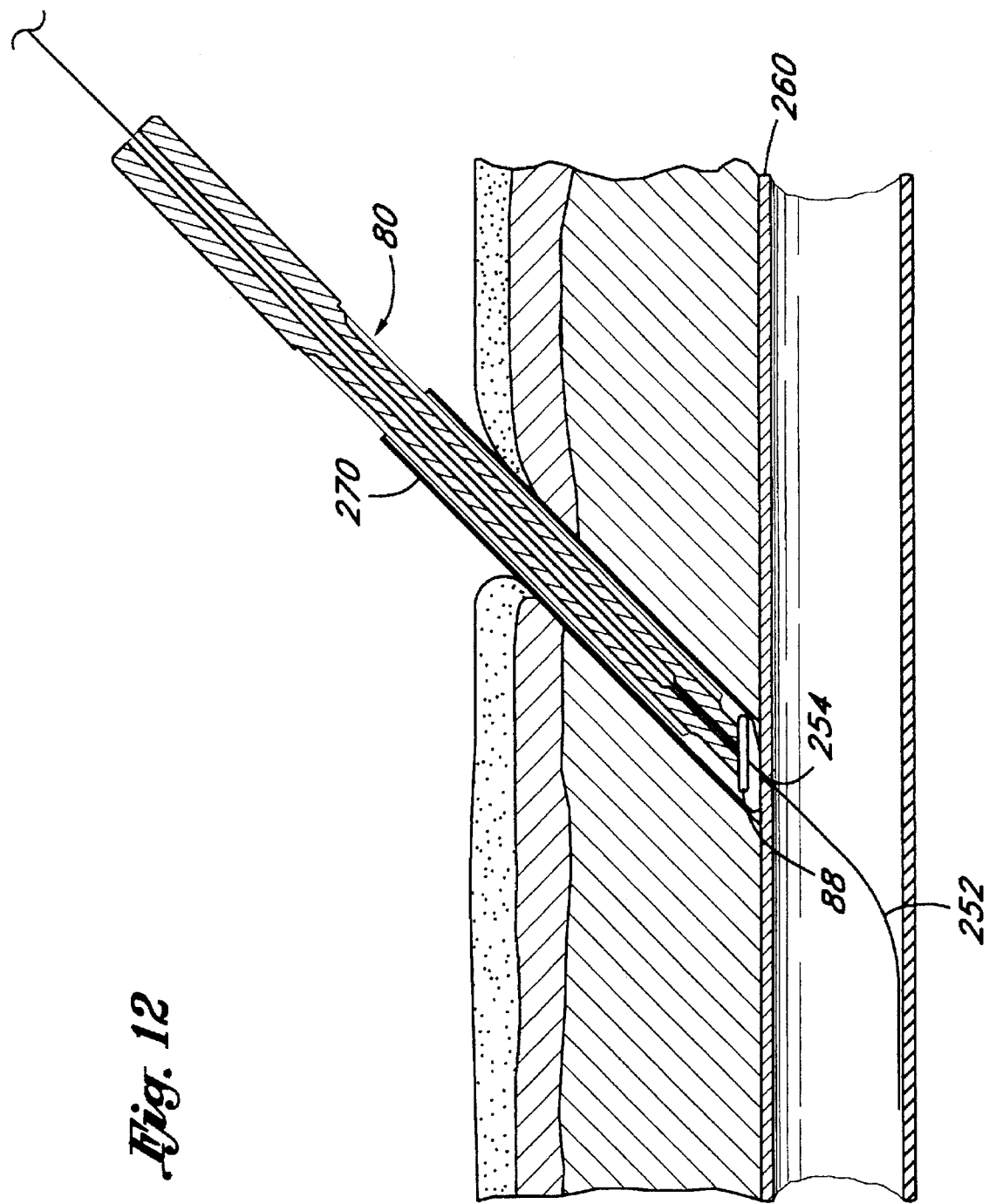
FIG. 12 is a schematic representation as in FIG. 11, with a vascular patch applicator advancing distally through the introducer cannula towards a vascular perforation.

At the point in the procedure illustrated at FIG. 11, the site is prepared for the application of an adhesive patch 88. Patch 88 is preferably secured to a patch applicator 80, as has been previously discussed. Attachment of the patch 88 to the applicator 80 can be accomplished such as through the use of a relatively weak adhesive bond or mechanical interfitting. In one embodiment, the patch 88 is preassembled onto the applicator 80, such as at the point of manufacture, by placing a relatively short shipping guidewire through the patch and into the guidewire lumen of applicator 80. This shipping guidewire may be provided with a distal anchor, such as a T or other configuration, to prevent the patch 88 from advancing off the end of the shipping guidewire. The proximal end of the shipping guidewire extends into the guidewire lumen and possibly out the proximal end of the applicator 80. When ready for use, the shipping guidewire can be removed by gripping the anchor portion or other structure and pulling it from the guidewire lumen. The proximal end of the procedure guidewire 252 then threaded into the patch 88 and distal end of applicator 80 as illustrated in FIG. 12.

Once a patch 88 is positioned on a patch surface 86 of a patch applicator 80, adhesive can be applied to the patch in any of a variety of ways. In accordance with one aspect of the present invention, the adhesive is applied using an adhesive delivery kit of the type illustrated in FIG. 6. Alternatively, adhesive can be manually applied to the tissue contacting surface of the patch 88 such as by the use of a squeeze tube, dropper, or other structure by the medical personnel at the time of the procedure. As a further alternative, any of the adhesive applicators disclosed herein can be used in the present method, without implanting a vascular patch.

In a typical procedure, the proximal end of a guidewire 252 extends through the perforation and out of the cannula 270. This may be a guidewire inserted for the purpose of the vascular patch procedure, or, more likely is the guidewire which was utilized in the original catherization. The patch applicator 80 having the patch 88 thereon is advanced over the proximal end of the guidewire, and advanced down the guidewire towards the patient. If the adhesive is manually applied to the patch, that application may be accomplished following threading the patch 88 applicator 80 onto the guidewire.

The operator then advances the applicator 80 along the guidewire and through the cannula 270 until the patch 88 contacts the vascular wall 260 without penetrating the perforation 254. See FIG. 12. The operator tactily feels and recognizes when the patch 88 contacts the ablumenal surface of the vessel wall 260. If other embodiments of the adhesive applicator disclosed herein are used, adhesive is expressed onto the surface of the applicator as will be understood in view of the previous disclosure herein.

As an alternative to tactile feedback once the introducer 270 has been properly positioned, the applicator 80 can be provided with visual or mechanical indicia which indicate that the appropriate depth has been reached. For example, applicator 80 can be provided with a mark or line around its circumference indicating the axial depth to which it should be advanced in a distal direction, before the mark disappears within introducer 270. Similarly, the applicator 80 can be advanced distally into the cannula 270 until a physical stop on the applicator 80 reaches the proximal end of the introducer 270.

The operator thereafter withdraws the applicator 80 from the cannula 270 after applying the patch 88 and tissue adhesive. The tissue compresses around the deposited patch 88 and percutaneous perforation. The tissue may be taped or bandaged subsequently to facilitate the physiological healing of the muscular and cutaneous tissue at the access site.

Although the present invention has been described in terms of certain preferred embodiments, other embodiments can be readily devised by one with skill in the art in view of the foregoing, which will also use the basic concepts of the present invention. Accordingly, the scope of the present invention is to be defined by reference to the following claims.

What is claimed is:

1. A method of closing a vascular perforation in a vessel wall of the type produced during a percutaneous transluminal catheterization procedure, comprising the steps of:

locating a percutaneous skin entrance site produced for the transluminal catheterization procedure;

introducing a tubular cannula through the skin entrance site and advancing the tubular cannula to bring it into contact with the surface of the wall surrounding the perforation;

providing an applicator which carries a patch;

applying a tissue adhesive to said patch so that said tissue adhesive is positioned between said patch and the surface of the vessel wall;

inserting said applicator carrying said patch and said tissue adhesive into the cannula; and adhering said patch to the surface of the wall surrounding the perforation to seal the perforation.

2. A method as in claim 1, wherein said adhesive is selected from the group of tissue adhesives consisting of methyl cyanoacrylate, ethyl cyanoacrylate, n-propyl cyanoacrylate, isopropyl cyanoacrylate, n-butyl cyanoacrylate, isobutyl cyanoacrylate, n-amyl cyanoacrylate, isoamyl cyanoacrylate, 3-acetoxypropyl cyanoacrylate, 2-methoxypropyl cyanoacrylate, 3-chloropropyl cyanoacrylate, benzyl cyanoacrylate, phenyl cyanoacrylate, alkenyl cyanoacrylate, butyl-2-cyanoacrylate, alkoxyalkyl 2-cyanoacrylates, fluorinated 2-cyanoacrylates and combinations thereof.

3. A method of closing a vascular perforation of the type produced during a percutaneous transluminal catheterization procedure, comprising the steps of:

locating a subcutaneous perforation in a vessel wall;

exposing the perforation together with the surface of the wall surrounding the perforation; and adhering a patch to the surface of the wall surrounding the perforation to seal the perforation; wherein said exposing step further comprises inserting an introducer sheath through the perforation and into the vessel, said sheath having a pressure sensor thereon;

sensing the pressure within the vessel;

withdrawing the introducer sheath from the vessel while monitoring the pressure within the vessel;

ceasing withdrawal of the introducer sheath once the pressure sensor detects a significant decrease in pressure;

percutaneously inserting a tubular cannula over said introducer sheath and positioning the distal end of the tubular cannula adjacent the vascular wall; and withdrawing said introducer sheath from said tubular cannula.

4. A method as in claim 3, wherein said percutaneously inserting a tubular cannula step comprises percutaneously inserting the cannula towards the vascular perforation at an angle of about 30° to the vessel wall.

5. A method as in claim 3, wherein said exposing step comprises exposing a circular area on the surface of the wall.

6. A method as in claim 3, wherein said circle has a diameter of about 3 mm.

7. A method as in claim 3, wherein said inserting an introducer sheath step is accomplished by inserting an introducer sheath over a guidewire.

8. A method as in claim 3, further comprising the step of providing a patch applicator and using the patch applicator to advance a patch to the surface of the wall prior to said adhering step.

9. A method as in claim 8, further comprising the step of applying an adhesive to the patch.

10. A method as in claim 9, wherein the adhesive comprises a cyanoacrylate.

11. A method of closing a vascular perforation of the type produced during a percutaneous transluminal procedure, comprising the steps of:

locating a perforation in a vessel wall;

percutaneously advancing a tubular cannula towards the perforation to expose the perforation together with the surface of the wall adjacent the perforation;

providing a vascular patch and a patch applicator;

advancing the patch along a guidewire and through the tubular cannula using the patch applicator; and adhering the patch to the surface of the wall to seal the perforation.

12. A method as in claim 11, further comprising the step of applying an adhesive to the patch prior to the advancing the patch step.

13. A method as in claim 12, wherein the applying an adhesive step comprises applying an ethyl cyanoacrylate or a butyl-2-cyanoacrylate based adhesive.

14. A method as in claim 11, further comprising the step of introducing a guidewire through the perforation and into the vessel, prior to the percutaneously advancing the tubular cannula step.

15. A method as in claim 11, wherein the adhering the patch to the surface of the wall step comprises advancing the patch through the tubular cannula until tactile feedback is received indicating that the patch is in contact with the vessel wall.

16. A method as in claim 11, further comprising the step of applying a thrombogenic agent to the patch prior to the advancing the patch step.

* * * * *